United States Patent
Lakowicz et al.

(10) Patent No.: US 7,989,220 B2
(45) Date of Patent: Aug. 2, 2011

(54) METAL-ENHANCED FLUORESCENCE FOR POLARIZATION-BASED AFFINITY ASSAYS

(75) Inventors: Joseph R. Lakowicz, Ellicott City, MD (US); Henryk Szmacinski, Ellicott City, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 12/427,722

(22) Filed: Apr. 21, 2009

(65) Prior Publication Data

US 2009/0275145 A1 Nov. 5, 2009

Related U.S. Application Data

(60) Provisional application No. 61/047,089, filed on Apr. 22, 2008.

(51) Int. Cl.
*G01N 33/553* (2006.01)
(52) U.S. Cl. ..................................................... 436/525
(58) Field of Classification Search .................. None
See application file for complete search history.

(56) References Cited

U.S. PATENT DOCUMENTS

| | | | |
|---|---|---|---|
| 6,632,613 B1 | 10/2003 | Wei et al. | |
| 7,217,518 B2 | 5/2007 | Sekar et al. | |
| 2004/0058458 A1* | 3/2004 | Anker et al. | 436/526 |
| 2009/0045351 A1* | 2/2009 | Smolyaninov et al. | 250/458.1 |

OTHER PUBLICATIONS

Bharadwaj, Palash and Novotny, Lukas, Spectral dependence of single molecule fluorescence enhancement, journal, Oct. 12, 2007, pp. 14266-14274, vol. 15, No. 21, Optical Society of America, United States.
Blanco, L.A. and García De Abajo, F.J, Spontaneous light emission in complex nanostructures, journal, May 28, 2004, pp. 1-12, vol. 69, No. 205414, Physical Review B, The American Physical Society, United States.
Das, Puma and Metiu, Horia, Enhancement of molecular fluorescence and photochemistry by small metal particles, journal, Jun. 4, 1985, pp. 4680-4687, vol. 89, No. 22, The Journal of Physical Chemistry, American Chemical Society, United States.
Elghanian, Robert, Storhoff, James J., Mucic, Robert C., Letsinger, Robert L., and Mirkin, Chad A., Selective Colorimetric Detection of Polynucleotides Based on the Distance-Dependent Optical Properties of Gold Nanoparticles, magazine, Aug. 22, 1997, pp. 1078-1081, vol. 277, Science, The American Association for the Advancement of Science, Washington D.C., United States.
Fang, Bin, Gao, Yingchun, Li, Maoguo, Wang, Guangfeng and Li, Yongxin, Application of Functionalized Ag Nanoparticles for the Determination of Proteins at Nanogram Levels Using the Resonance Light Scattering Method, journal, May 21, 2004, pp. 81-86, vol. 147, Microchimica Acta, Springer-Verlag, Austria.
Garoff, S., Weitz, D.A., Alvarez, M.S. and Gersten, J.I., Electrodynamics at rough metal surfaces: Photochemistry and luminescence of adsorbates near metal-island films, journal, Dec. 1, 1984, pp. 5189-5200, vol. 81, No. 11, Journal of Chemical Physics, The American Institute of Physics, United States.
Gerber, Sebastian, Reil, Frank, Hohenester, Ulrich, Schlagenhaufen, Thomas, Krenn, Joachim R. and Leitner, Alfred, Tailoring light emission properties of fluorophores by coupling resonance-tuned metallic nanostructures, journal, Feb. 6, 2007, pp. 1-4, vol. 75, No. 073404, Physical Review B, The American Physical Soceity, United States.
Gersten, J. and Nitzan, A.J., Spectroscopic properties of molecules interacting with small dielectric particles, journal, Aug. 1, 1981, pp. 1139-1152, vol. 75, No. 3, Journal of Chemical Physics, The American Institute of Physics, United States.
Gryczynski, Zygmunt, Lukomska, Joanna, Lakowicz, Joseph R., Matveeva, Evgenia G., and Gryczynski, Ignacy, Depolarized light scattering from silver nanoparticles, journal, Feb. 14, 2006, pp. 189-192, vol. 421, Chemical Physics Letters, Elsevier B.V., Netherlands.
Guzatov, D.V. and Klimov, V.V., Radiative decay engineering by triaxial nanoellipsoids, journal, Jul. 28, 2005, pp. 341-346, vol. 412, Chemical Physics Letters, Elsevier B.V., Netherlands.
Hirsch, L.R., Jackson, J.B., Lee, A., Halas, N.J., and West, J.L., A Whole Blood Immunoassay Using Gold Nanoshells, journal, Apr. 9, 2003, pp. 2377-2381, vol. 75, No. 10, Analytical Chemistry, American Chemical Society, United States.
Kawski, Ph.D., D.Sc., Alfons, Fluorescence Anisotrophy: Theory and Applications of Rotational Depolarization, journal, 1993, pp. 459-529, vol. 23, No. 6, Critical Reviews in Analytical Chemistry, CRC Press, Inc., United States.
Kumar, Sonia, Harrison, Nathan, Richards-Kortum, Rebecca and Sokolov, Konstantin, Plasmonic Nanosensors for Imaging Intracellular Biomarkers in Live Cells, journal, Apr. 17, 2007, pp. 1338-1343, vol. 7, No. 5, Nano Letters, American Chemical Society, United States.

(Continued)

*Primary Examiner* — Ann Lam
(74) *Attorney, Agent, or Firm* — Evans & Molinelli PLLC; Eugene Molinelli

(57) ABSTRACT

A method and kit for determining the quantity of an analyte include providing a functionalized substrate and a reagent. The functionalized substrate includes metallic nanoparticles and a plurality of substantively identical bioactive target molecules affixed to a substrate. The bioactive target molecule binds to a particular analyte. The reagent includes identical detection molecules. Each detection molecule includes a fluorophore, and binds to a particular analyte or competes with a particular analyte for binding to the target molecule. The functionalized substrate is contacted to a test sample and the reagent. The functionalized substrate and a covering solution are exposed to polarized electromagnetic waves that excite the fluorophore. A quantity of the particular analyte in the test sample is determined based on measuring polarization anisotropy of fluorescent emissions from the substrate and the covering solution.

15 Claims, 8 Drawing Sheets

OTHER PUBLICATIONS

Kümmerlen, J., Leitner, A., Brunner, H., Aussenegg, F.R. and Wokaun, A., Enhanced dye fuorescence over silver island films: analysis of the distance dependence, journal, Jun. 21, 1993, pp. 1031-1046, vol. 80, No. 5, Molecular Physics, Taylor & Francis Ltd., United Kingdom.

Lakowicz, Joseph R., Principles of Fluorescence Spectroscopy, book, 2006, pp. 353-382, Third Edition, Springer Science, New York, United States.

Lakowicz, Joseph R., Shen, Yibing, D'Auria, Sabato, Malicka, Joanna, Fang, Jiyu, Gryczynski and Gryczynski, Ignacy, Radiative Decay Engineering, journal, Jan. 15, 2002, pp. 261-277, vol. 301, Analytical Biochemistry, Elsevier Science, United States.

Lukomska, Joanna, Malicka, Joanna, Gryczynski, Ignacy and Lakowicz, Joseph R., Fluorescence Enhancements on Silver Colloid Coated Surfaces, journal, Mar. 11, 2004, pp. 417-423, vol. 14, No. 4, Journal of Fluorescence, Plenum Publishing Corporation, United States.

Malicka, Joanna, Gryczynski, Ignacy, Fang, Jiyu, Kusba, Jozef and Lakowicz, Joseph R., Photostability of Cy3 and Cy5-Labeled DNA in the Presence of Metallic Silver Particles, journal, Apr. 15, 2002, pp. 439-447, vol. 12, Nos. 3/4, Journal of Fluorescence, Plenum Publishing Corporation, United States.

Malicka, Joanna, Gryczynski, Ignacy, Gryczynski, Zygmunt and Lakowicz, Joseph R., Effects of fluorophore-to-silver distance on the emission of cyanine-dye-labeled oligonucleotides, journal, 2003, pp. 57-66, vol. 315, Analytical Biochemistry, Elsevier Science, United States.

Maliwal, Badri P., Malicka, Joanna, Gryczynski, Ignacy, Gryczynski, Zygmunt and Lakowicz, Joseph R., Fluorescence Properties of Labeled Proteins Near Silver Colloid Surfaces, journal, Feb 21, 2003, pp. 585-594, vol. 70, No. 4, Biopolymers (Biospectroscopy), Wiley Periodicals, Inc., United States.

Metveeva, Evgenia G., Gryczynski, Ignacy, Barnett, Anne, Leonenko, Zoya, Lakowicz, Joseph R., and Gryczynski, Zygmunt, Metal particle-enhanced fluorescent immunoassays on metal mirrors, journal, Jan. 26, 2007, pp. 239-245, vol. 363, Analytical Biochemistry, Elsevier Inc., United States.

Mertens, H., Koenderink, A.F. and Polman, A., Plasmon-enhanced luminescence near noble-metal nanospheres: Comparison of exact theory and an improved Gersten and Nitzan model, journal, Sep. 21, 2007, pp. 1-12, vol. 76, No. 115123, Physical Review B, The American Physical Society, United States.

Nam, Jwa-Min, Thaxton, C. Shad and Mirkin, Chad A., Nanoparticle-Based Bio-Bar Codes for Ultrasensitive Detection of Proteins, magazine, Sep. 26, 2003, pp. 1884-1886, vol. 301, Science, The American Association for the Advancement of Science, Washington D.C., United States.

Ni, Fan and Cotton, Therese M., Chemical Procedure for Preparing Surface-Enhanced Raman Scattering Active Silver Films, journal, May 1, 2002, pp. 3159-3163, vol. 58, Analytical Chemistry, American Chemical Society, United States.

Sipior, Jeffrey, Carter, Gary M., Lakowicz, Joseph R. and Rao, Govind, Single quantum well light emitting diodes demonstrated as excitation sources for nanosecond phase-modulation fluorescence lifetime measurements, journal, Aug. 26, 1996, pp. 3795-3798, vol. 67, No. 11, Review of Scientific Instruments, The American Institute of Physics, United States.

Sokolov, Konstantin, Chumanov, George and Cotton, Therese M., Enhancement of Molecular Fluorescence near the Surface of Colloidal Metal Films, journal, Aug. 8, 1998, pp. 3898-3905, vol. 70, No. 18, Analytical Chemistry, American Chemical Society, United States.

Storhoff, James J., Lucas, Adam D., Garimella, Viswanadham, Bao, Paul Y. And Müller, Uwe R., Homogeneous detection of unamplified genomic DNA sequences based on colorimetric scatter of gold nanoparticle probes, journal, May 30, 2004, pp. 883-887, vol. 22, No. 7, Nature Biotechnology, Nature Publishing Group, United States.

Szmacinski, Henryk and Chang, Qing, Micro- and Sub-nanosecond Lifetime Measurements Using a UV Light-Emitting Diode, journal, 2000, pp. 106-109, vol. 54, Issue 1, Society for Applied Spectrocopy, United States.

Wang, Zhenxin, Lee, Jason, Cossins, Andrew R. and Brust, Mathias, Microarray-Based Detection of Protein Binding and Functionality by Gold Nanoparticle Probes, journal, Sep. 1, 2005, pp. 5770-5774, vol. 77, No. 17, Analytical Chemistry, American Chemical Society, United States.

Weitz, D.A., Garoff, S., Gersten, J.I. and Nitzan, A., The enhancement of Raman scattering, resonance Raman scattering, and fluorescence from molecules adsorbed on a rough silver surface, journal, May 1, 1983, pp. 5324-5338, vol. 78, No. 9, Journal of Chemical Physics, the American Institute of Physics, United States.

* cited by examiner

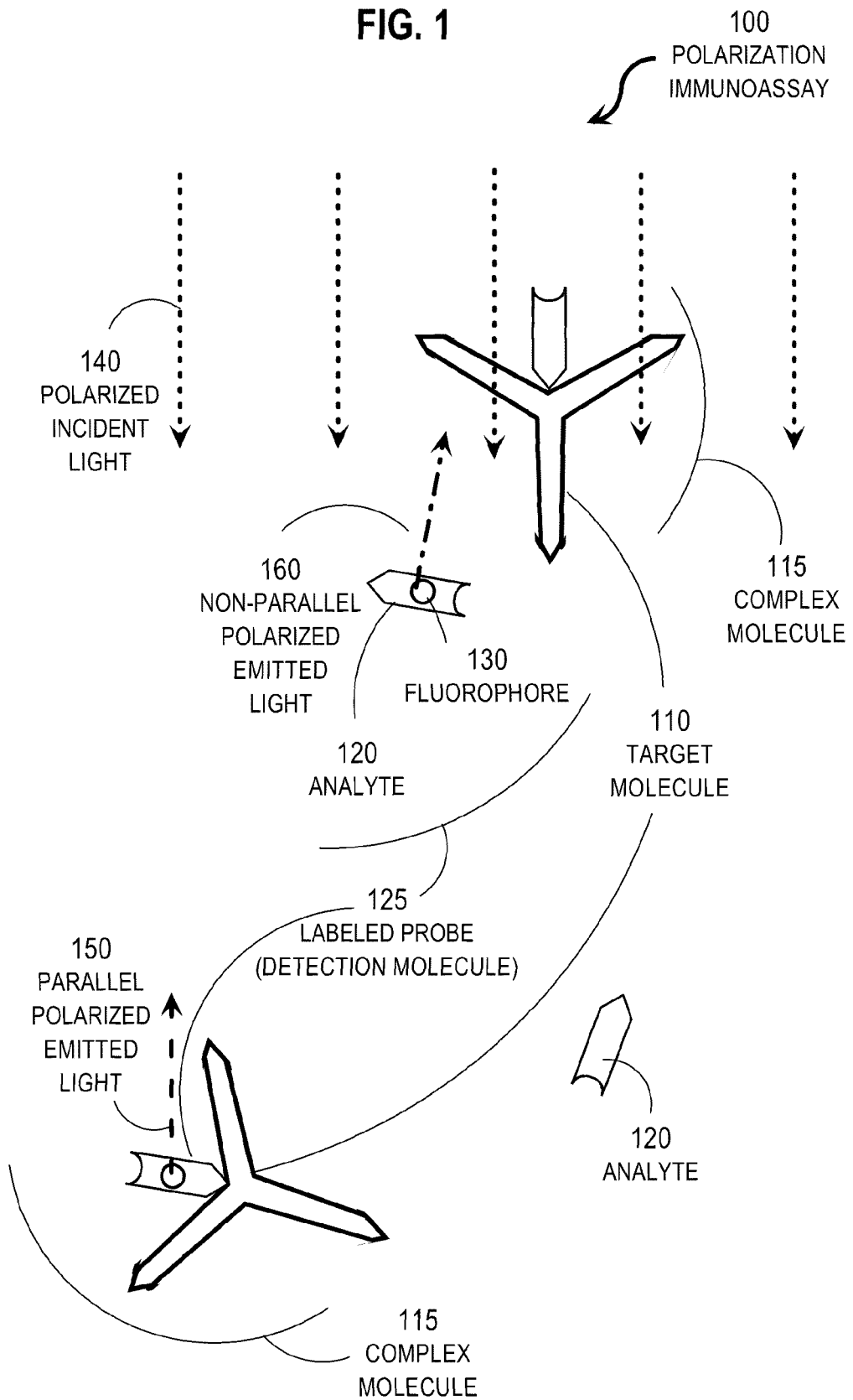

200 FUNCTIONALIZED SUBSTRATE
220 FILM OF METAL NANOPARTICLES
230 LAYER OF FIXED BIOACTIVE MOLECULES
210 GLASS SUBSTRATE
212 WELLS
202 REGION A

202 REGION A
222 METAL NANOPARTICLES
232 FIXED BIOACTIVE MOLECULES
210 GLASS SUBSTRATE

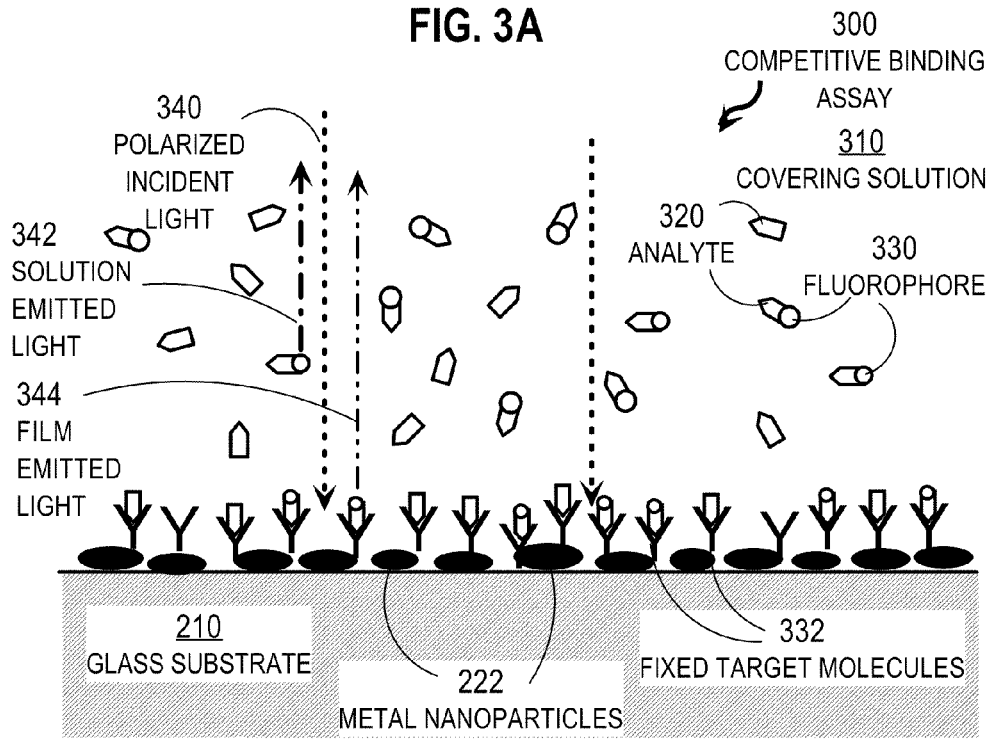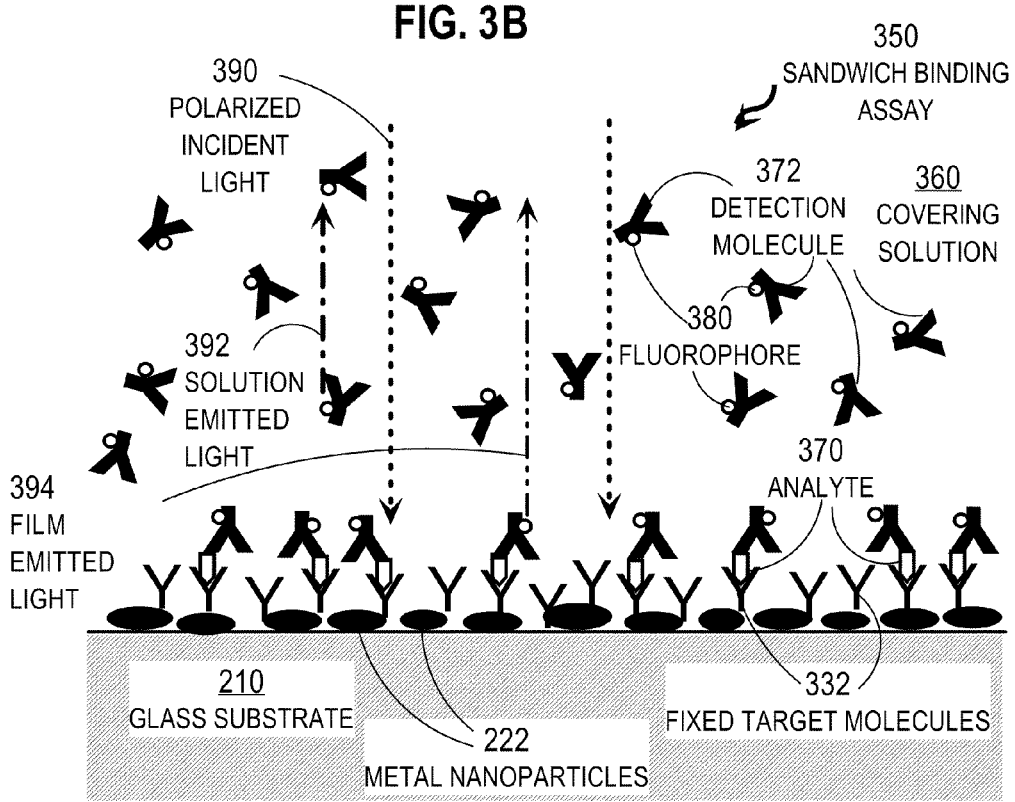

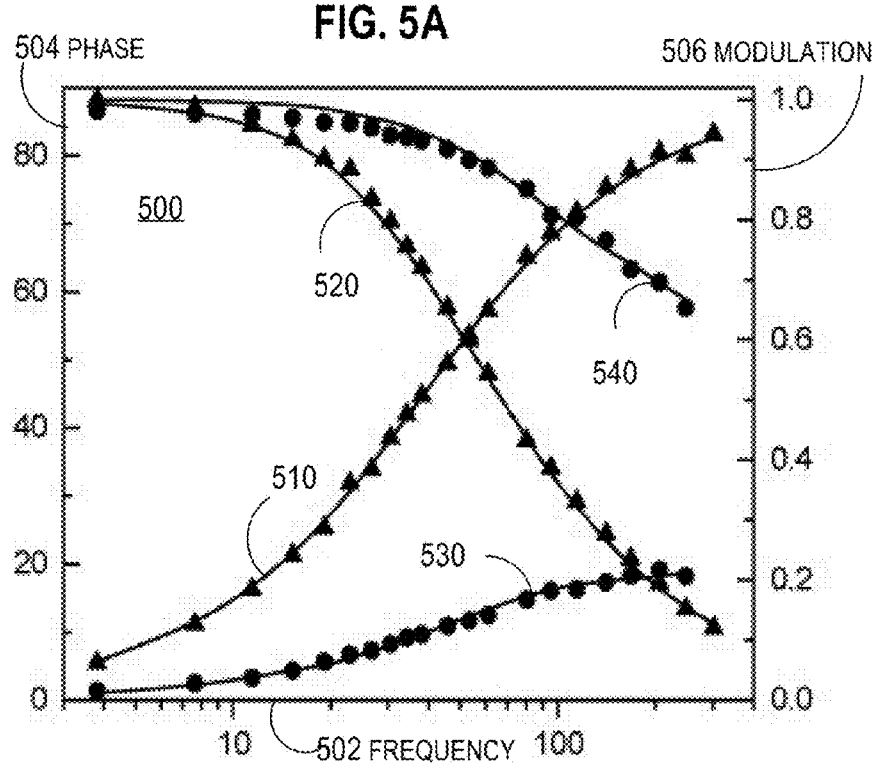
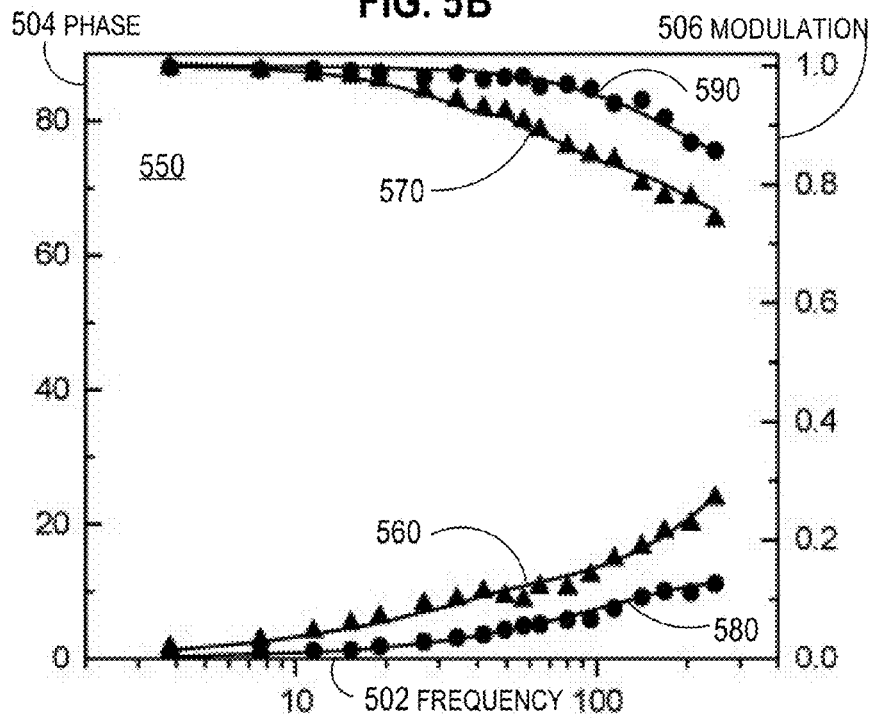

METAL-ENHANCED FLUORESCENCE FOR POLARIZATION-BASED AFFINITY ASSAYS

CROSS-REFERENCE TO RELATED APPLICATIONS

This application claims benefit of Provisional Appln. 61/047,089, filed Apr. 22, 2008, the entire contents of which are hereby incorporated by reference as if fully set forth herein, under 35 U.S.C. §119(e).

STATEMENT OF GOVERNMENTAL INTEREST

This invention was made with government support under EB006521 and HG002655 awarded by the National Institutes of Health (NIH). The government has certain rights in the invention.

BACKGROUND OF THE INVENTION

1. Field of the Invention

The present invention relates to polarization-based affinity assays.

2. Description of the Related Art

In affinity assays, a known quantity of a labeled probe competes with or binds to an unknown quantity of unlabeled analyte at binding sites on a target molecule for which the analyte has an affinity. The labeled probe that is bound to the target molecule presents a different measurable phenomenon than the labeled probe that is unbound. Calibration curves relate the presence or quantity of the analyte to the relative amount of bound to unbound labeled probe. The calibration curves are generated by measuring the relative amounts of bound and unbound labeled probe in the presence of known quantities of analyte. In competitive binding assays the probe is the same as the analyte or is another entity that competes for the same binding sites on the target molecule. In sandwich binding assays the probe binds to the analyte that is bound to the target molecule. In immunoassays, the analyte is an antigen and the target molecule is an antibody.

In fluorescent affinity assays, the probe is labeled with a fluorophore. A fluorophore is a functional group in a molecule which absorbs electromagnetic waves at a specific wavelength and subsequently emits electromagnetic waves at a different specific wavelength. The electromagnetic waves involved in some fluorophores have wavelengths that are in or near the visible band, and are called light hereinafter.

Polarized electromagnetic waves have a particular directional component for the varying electric field. When linearly polarized light is used to stimulate fluorescence, the light emitted is also linearly polarized. This phenomenon is generally termed fluorescence polarization.

Fluorescence polarization immunoassay (FPIA) is a competitive binding assay that takes advantage of changes in degree of polarization of emitted fluorescent light when a fluorophore-labeled antigen is bound to an antibody. In traditional FPIA, an observable polarization change relies on labeling relatively small antigens with small fluorophores that display relatively long lifetime emissions to obtain depolarized fluorescence from the unbound probe as it rotates in solution at a rapid rate (with a corresponding short rotational correlation time). A small antigen is usually less than 10 kiloDaltons (kDa, where 1 kDa=103 Daltons, and 1 Dalton is a basic unit of atomic weight approximately equal to one twelfth the atomic weight of Carbon 12). An example of a long lifetime fluorophore is Fluorescein with a lifetime of about 4 nanosecond (ns, 1 ns=$10^{-9}$ seconds). The FPIAs detect the increase in emission polarization when a small probe-fluorophore conjugate binds to a large target molecule that rotates more slowly in solution. The higher the concentration of unlabeled antigen present in a test sample (e.g., from a patient) mixed with the labeled probes, the less bound labeled antigen is present and, consequently, the lower the polarization of the fluorescent light emission.

A disadvantage of the traditional FPIA is the requirement that the labeled probe be much smaller than the target molecules. This restriction eliminates many probes of interest. Since the probes are the same as the analyte in most competitive binding assays, this restriction also eliminates many analytes of interest. For example, molecules of size like streptavidin for which many fluorophore conjugates are commercially available as labels binds to many target biotinylated molecules of interest. Such molecules can not be regarded as conventional polarization probes because of their large size that precludes displaying useful changes in polarization values when bound in solution to biotinylated bovine serum albumin (BSA-bt) as a target molecule. The molecular weight of streptavidin, of about 66 kDa, results in a large rotational correlation time that is too long, when unbound, to be detectably depolarized.

SUMMARY OF THE INVENTION

Novel methods and kits are provided for determining the quantity of an analyte using polarization fluorescence.

In a first set of embodiments, an assay method includes providing a functionalized substrate and a reagent. The functionalized substrate includes metallic nanoparticles and bioactive target molecules affixed to a substrate. The bioactive target molecule binds to a particular analyte. The reagent includes detection molecules that include a fluorophore. The detection molecule binds to the particular analyte or competes with the particular analyte for binding to the target molecule. The functionalized substrate contacts a test sample and the reagent. The functionalized substrate and a covering solution resulting from such contact are exposed to polarized electromagnetic waves that excite the fluorophore. A quantity of the particular analyte in the test sample is determined based on measuring polarization anisotropy of fluorescent emissions from the substrate and the covering solution.

In another set of embodiments, a fluorescence polarization affinity assay kit for an analyte includes a metal film substrate, a solution and a reagent. The metal film substrate includes metallic nanoparticles affixed to a substrate. The solution includes a bioactive target molecule that binds to a particular analyte. The target molecule includes a ligand for affixing to the metal film substrate to functionalize the substrate. The reagent includes multiple essentially identical detection molecules that each includes a fluorophore. The detection molecule binds to the particular analyte or competes with the particular analyte for binding to the target molecule. The kit is used to produce a functionalized substrate and covering solution that is subjected to polarization anisotropy measurements that determine the quantity of the analyte in a test sample.

BRIEF DESCRIPTION OF THE DRAWINGS

The present invention is illustrated by way of example, and not by way of limitation, in the figures of the accompanying drawings and in which like reference numerals refer to similar elements and in which:

FIG. 1 is a block diagram that illustrates a fluorescence polarization immunoassay (FPIA) during operation;

FIG. 3A is a block diagram that illustrates an example MEF-P competitive binding assay during operation, according to an embodiment;

FIG. 3B is a block diagram that illustrates an example MEF-P sandwich binding assay during operation, according to an embodiment;

FIG. 5A is a graph that illustrates example intensity decays for a detection molecule that includes a Fluorescein fluorophore, both free in solution and bound to a metal film functionalized substrate, according to an embodiment;

FIG. 5B is a graph that illustrates example intensity decays for a detection molecule that includes a DY547-SA fluorophore, both in solution and bound to a metal film functionalized substrate, according to an embodiment;

DETAILED DESCRIPTION

Figure 2A:
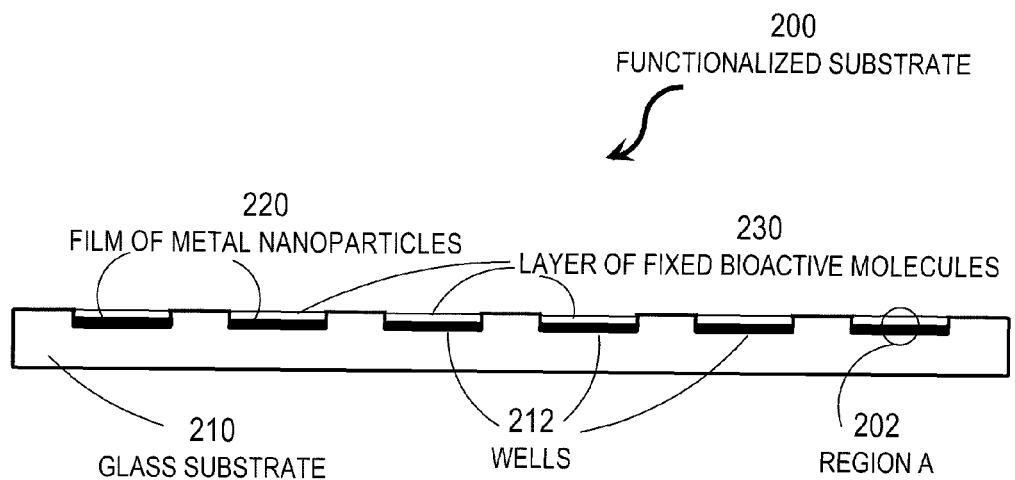
FIG. 2A is a block diagram that illustrates an example functionalized substrate for a metal enhanced fluorescence polarization (MEF-P) assay, according to an embodiment.

A method and apparatus for determining a quantity of analyte in a test sample are described. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

The inventors have discovered a surprising increase in intensity and decrease in polarization of fluorescent emissions in the presence of metal nanoparticles. Subsequently they determined how these properties can be used to design a new family of assays for analytes that have an affinity for a known target molecule.

Some embodiments of the invention are described below in the context of immunoassays in the presence of silver island films. In immunoassays the analyte is an antigen and target molecule is a corresponding antibody. However, the invention is not limited to this context. In other embodiments any biological entity may be the analyte and any molecule with analyte affinity may be the target molecule and any metal may be used for the nanoparticles. Furthermore, any fluorophore may be used to label a detection molecule used to determine binding of analyte to target molecule.

1. Definitions

As used in this description, the following terms have the meanings given here.

analyte a component of a sample for which a quantity is to be determined, including but not limited to a polymer, a ligand, an antigen, an antibody, a protein, a peptide, DNA, RNA, oligonucleotide, a virus or a bacterium.

anisotropy angular dependence of a physical property. Polarization anisotropy is angular dependence of electromagnetic wave polarization.

anisotropy measure, r a measure of the relative intensity in two perpendicular directions of the electric field of electromagnetic (em) waves, which is defined by the equation:

$$r=(I1-I2)/(I1+2*I2)$$

where I1 is the intensity of em waves with electric fields in a first direction and I2 is the intensity of em waves with electric fields in a second direction perpendicular to the first. For fluorescence anisotropy, the first direction is parallel to the electric field in the polarized em waves that excite fluorescence.

assay a method to determine the quantity (e.g., the presence, absence, or concentration) of one or more components called analytes in a test sample.

assay kit a collection of materials to be used in an assay.

BSA-bt biotinylated bovine serum albumin, an example target molecule.

concentration a fraction of a sample by weight or volume which is due to a component of the sample.

detection molecule a molecule labeled with a fluorophore that is used to detect binding of an analyte to a target molecule by binding to the analyte or by competing with the analyte for binding sites on the target molecule. Also called a probe-fluorophore conjugate or probe-dye conjugate.

fluorophore a functional group in a molecule which absorbs electromagnetic waves at a specific wavelength and subsequently emits electromagnetic waves at a different specific wavelength. Fluorophores include, but are not limited to, fluoresceins, eosin, coumarines, rhodamines, cyanines, benzophenoxazines, phycobiliproteins or fluorescent proteins.

functionalized substrate a substrate that is conditioned to perform a particular function by deposition of layers of one or more types of molecules, including a glass slide coated with bioactive molecules that facilitate fixing of an analyte to the substrate.

ligand a functional group in a molecule which binds to a metal, generally involving formal donation of one or more of its electrons. Metal-ligand bindings range from covalent bonds to electrostatic attraction between ions (ionic bonding).

probe a molecule that is used to detect binding of an analyte to a target molecule by binding to the analyte or by competing with the analyte for binding sites on the target molecule (the portion of a detection molecule excluding the fluorophore). Probes include, but are not limited to, a polymer, a ligand, an antigen, an antibody, a protein, an oligomer, a protein, a peptide, DNA, RNA or an oligonucleotide.

probe-fluorophore conjugate A detection molecule.

light electromagnetic (em) waves in a visible portion of the electromagnetic spectrum, which includes wavelengths from about 300 to about 800 nanometers (nm, 1 nm=$10^{-9}$ meters).

nanoparticles particles each having a dimension in a size range from 1 to 1000 nanometers.

plasmon an oscillation of free electron density in a metal particle which can form waves on metal surfaces with the same electric fields and frequencies but shorter wavelengths than electromagnetic waves. Metal surface plasmons with frequencies in the visible spectrum can interact with light.

polarization measure, P a measure of the relative intensity in two perpendicular directions of components of the electric field in a beam of electromagnetic waves defined by the equation $$P=(I1-I2)/(I1+I2)$$

where I1 is the intensity of em waves with electric fields in a first direction and I2 is the intensity of em waves with electric fields in a second direction perpendicular to the first. For fluorescence polarization the first direction is parallel to the electric field in the polarized em waves that excite fluorescence. P is related to anisotropy r by the equation $$P=3r/(2+r)$$

Linearly polarized em waves electromagnetic waves in which the varying electric field is in a single direction.

reagent substance or compound consumed during a chemical reaction.

solution a liquid mixture.

streptavidin-dye conjugate the protein streptavidin labeled with one or more fluorophores, and thus an example detection molecule.

substrate a material on which a process is conducted target molecule a molecule which has an affinity for a particular analyte. Target molecules include, but are not limited to, a polymer, a ligand, an antigen, an antibody, a protein, a peptide, DNA, RNA, an oligonucleotide.

test sample a sample, such as a biological sample, with an unknown quantity of an analyte

1. Overview of FPIA

As stated in the background section, in a traditional fluorescence polarization immunoassay (FPIA), an observable polarization change relies on labeling relatively small antigens with small fluorophores that display relatively long lifetime emissions to obtain depolarized fluorescence from the unbound labeled probe as it rotates at a rapid rate (with a corresponding short rotational correlation time) compared to a labeled probe bound to a large target molecule.

FIG. 1 is a block diagram that illustrates a fluorescence polarization immunoassay (FPIA) 100 during operation as a competitive binding assay. FPIA 100 includes analyte molecules 120 (such as antigens), target molecules 110 (such as antibodies) and analyte molecules 120 labeled with fluorophore 130 (called detection molecules or labeled probes 125 or probe-fluorophore conjugates), all in solution. In solution, a molecule rotates at a rate that is inversely proportional to its molecular weight. Thus the larger target molecules 110 rotate more slowly than the smaller analyte 120 and detection molecules 125. A complex 115, formed when an analyte 120 bonds to a target molecule 110, rotates more slowly than an unbound analyte 120, 125. The solution depicted in FIG. 1 is formed by mixing a reagent that has a known amount of detection molecules 125 with a test sample that has an unknown amount of analyte 120 that is not labeled.

When exposed to polarized incident light 140, represented by dotted arrows, the bound detection molecule emits light 150, represented by dashed arrows, that is highly polarized in a direction parallel to the polarization of the incident light. However, the free (unbound) detection molecule emits light 160, represented by single-dot dashed arrows, that is not so highly polarized. This is the case if the lifetime of the fluorescent emission from the fluorophore is long compared to the rate of rotation of the unbound detection molecule. By measuring the relative amounts of parallel polarized emitted light 150 to the non-parallel polarized emitted light 160, the ratio of the number of bound detection molecules to the number of free detection molecules can be determined. The less polarized the emitted light, the higher the fraction of detection molecules that are free in solution compared to those that are bound to the target molecule. Fewer analytes labeled with fluorophores 130 bound to the target 110 indicates more unlabeled analyte is bound to the target molecules 110, which indicates a higher concentration of unlabeled analyte in the test sample.

A quantitative measure of the concentration of unlabeled analyte in the test solution is obtained using a calibration curve. A calibration curve is generated by measuring polarization of the emitted light with known amounts of both labeled and unlabeled analyte. The quantitative measure can be the presence or absence of the analyte in the test sample, or the concentration of the analyte.

For the conventional immunoassay to work, there are limits on the size of the analyte and the lifetime of the fluorophore emission. The molecule size and lifetime limits for useful polarization changes are related by the rotation rate, which is inversely related to the rotational correlation time. The slower the rotation rate, the longer the rotation correlation time. The rotational correlation time, $\tau_C$, is related to the molecular weight (MW) of molecule as given by Equation 1.

$$\tau_C = \frac{\eta MW}{RT} \tag{1}$$

where $\eta$ is the solution viscosity, MW the molecular weight, R the universal gas constant, and T is the temperature in degrees Kelvin (° K.).

The extent of polarization is quantified by an anisotropy measure. Anisotropy, r, is defined by Equation 2.

$$r=(I1-I2)/(I1+2*I2) \tag{2}$$

where I1 is the measured intensity of light in the fluorescent emissions that is polarized parallel to the incident excitation light (e.g., parallel to polarized incident light 140), and I2 is the measured intensity of light in the fluorescent emissions that is polarized perpendicularly to the incident light. When all the fluorescent emissions are parallel to the incident light, I2=0 and r=1.

A dominant cause of fluorescence depolarization is rotational diffusion of fluorophores. For the simplest case of a spherical rotor, this mode of depolarization is described by Equation 3.

$$r = \frac{r_0}{1 + \frac{\tau}{\tau_C}} \tag{3}$$

where $\tau$ is the fluorescence lifetime and $\tau_C$ is the rotational correlation time (the time for anisotropy to decrease 1/e of its limiting value) and $r_0$ is a photophysical constant of a particular fluorophore. For unbound detection molecules to have low anisotropy, it is desirable that $\tau_C \ll \tau$. Therefore fluorophores with long fluorescence lifetimes and detection molecules with short rotational correlation times (which implies low molecular weight) are desired.

Traditionally, the FPIAs relied on labeling relatively small biomolecules with similarly small fluorophores that display relatively long lifetimes (usually Fluorescein with about 4 nanoseconds, ns, where 1 ns=$10^{-9}$ seconds) to obtain depolarized fluorescence from the unbound labeled probe. Thus, traditional FPIAs performed with organic dyes that display lifetimes in the nanosecond range require low molecular weight molecules for the detection molecules, typically less than 10 kiloDaltons (kDa, where 1 kDa=$10^3$ Da and 1 Da=one twelfth of the mass of an unbound atom of Carbon-12 at rest and in its ground state). This severely limits the usefulness of these methods for large analytes and fluorophores with short fluorescence lifetimes.

2. MEF-P

Recently, several groups have begun using metallic nanostructures to generate fluorescence enhancements that have the potential for use in single molecule detection. The strong interaction between the free electrons in the metallic nanostructures and an incident electromagnetic field creates unique optical properties. Techniques to measure these properties include resonance light scattering (RLS), distance-dependent scattering properties of nanoparticles, or scattering and extinction properties of metal-dielectric nanoshells. Coupling these metallic nanoparticles with fluorescent probes also resulted in unique effects based on near-field interactions. When fluorophores are within 3-50 nm from the surface of the metallic nanostructures, a plasmon-fluorophore interaction occurs. A plasmon is an oscillation of free electron density in a metal particle which can form waves on metal surfaces with the same electric field frequencies but shorter wavelengths than interacting electromagnetic waves. Metal surface plasmons with frequencies in the visible spectrum can interact with light. Such plasmon-fluorophore interactions produce an observed reduction in the fluorescence lifetime through an increased radiative decay rate while also enhancing the fluorescence intensity through an increased excitation field and increased radiative decay rate. The effect has been called metal-enhanced fluorescence (MEF) or surface-enhanced fluorescence (SEF). The result is improved photostability of brighter fluorophores due to a decrease in the time the fluorophore stays in the excited state. It has also been observed that the fluorophores under MEF conditions are less susceptible to optical saturation. Theoretical calculations on surface enhanced fluorescence were also extensively published.

The inventors have discovered a surprising decrease in polarization of fluorescent emissions in the presence of metal nanoparticles. They have named this phenomenon metal enhanced fluorescence polarization (MEF-P). Subsequently, the inventors determined how this phenomenon can be used to design a new family of assays for analytes that have an affinity for a known target molecule and that do not have the limitations in analyte and fluorophore size or fluorophore lifetimes of traditional FPIA.

2.1 Effect of Metal Nanoparticles on Fluorescence Polarization

In this section are described the MEF-P observations made by the inventors that served as a basis for the MEF-P affinity assays described in more detail in later sections.

The previous reports on surface-enhanced fluorescence do not consider the level of emission polarization. Here is presented experimental data on anisotropy of surface-enhanced fluorescence. These experiments incorporate silver island films (SIFs) deposited on planar glass slides and several fluorophores conjugated to proteins that bind to the SIFs. The measurements included intensity, lifetime, and emission anisotropy for fluorophore-protein conjugates when those conjugates are free in solution and when bound to the SIFs substrates. The proteins are analogous to the probes and target molecules of an assay, as described in a later section. The observed effects form the basis for a new generation of fluorescence polarization based sensing, including embodiments as immunoassays.

2.1.1 Metal Nanoparticles Alone on Substrate

Silver island films (SIFs) were deposited on quartz substrate. A wet chemical deposition method was used to coat the substrate with the SIFs. The procedure has been described in Lakowicz, J. R.; Shen, Y.; Dauria, S.; Malicka, J.; Fang, J.; Gryczynski, Z.; Gryczynski, I. *Anal. Biochem.* 2002, 301, 261-277 and in Maliwal, B. P.; Malicka, J.; Gryczynski, Z.; Gryczynski, I.; Lakowicz, J. R. *Biopolymers (Biospectroscopy)* 2003, 70, 585-594, the entire contents of each of which are hereby incorporated by reference as if fully set forth herein. Briefly, the reduction of silver ions by D-glucose results in the deposition of the SIFs on the glass or quartz substrate. In previous experiments, the fluorescence enhancement achieved in the presence of the silver islands strongly depends on the silver particle surface morphology where silver islands and silver colloids were deposited on the glass surface. In the current experiments, the wet chemical deposition technique results in variable particle sizes and shapes. The size and shape variability, with particle sizes up to 500 nm and thicknesses of 50-100 nm, has been previously shown using atomic force microscopy. High density silver islands were deposited to limit the void areas between particles where fluorophores would not effectively interact with particle plasmons.

The extinction spectrum of silver islands film was measured using a single beam spectrophotometer (Hewlett-Packard model 8543). The polarization scattering spectra of the SIFs were measured using Varian fluorometer (Eclipse 4) in a synchronous mode, in which the excitation and emission monochromators were at the same wavelength.

Figure 6:
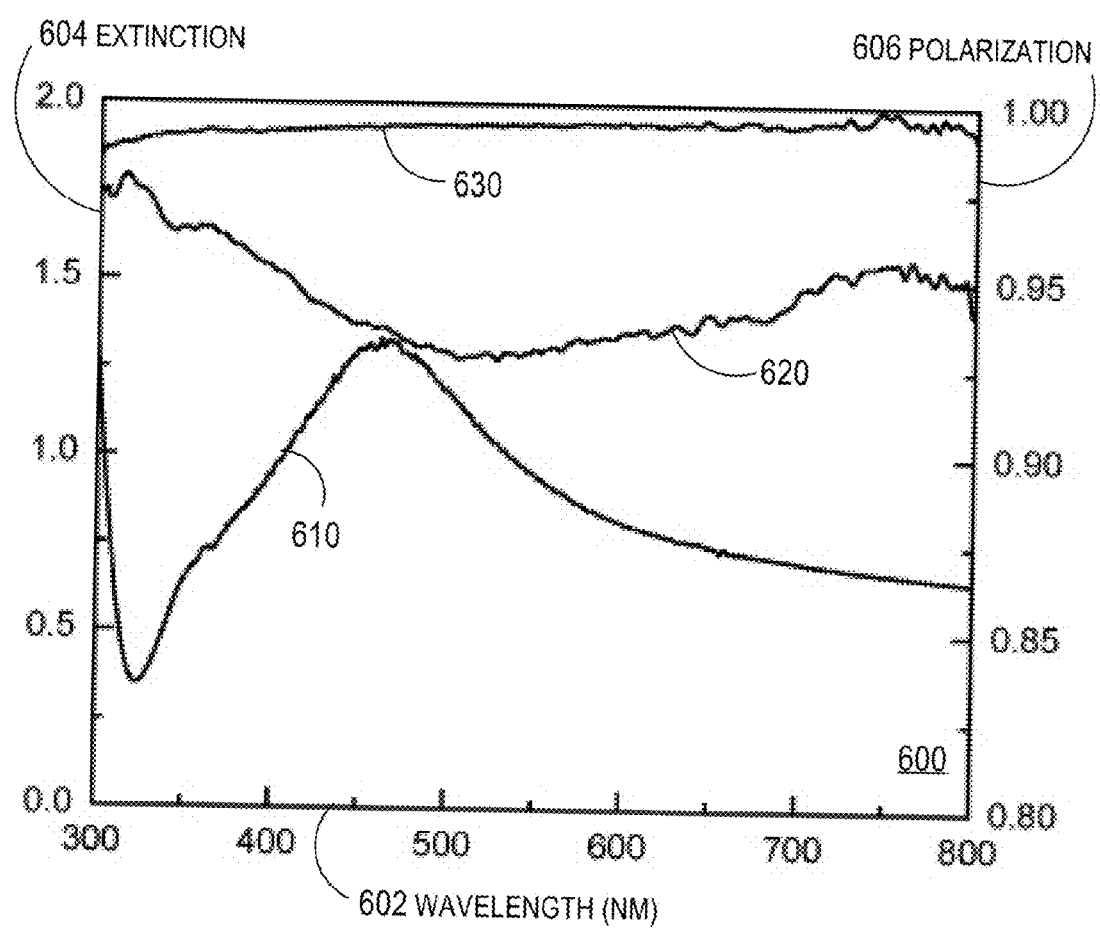
FIG. 6 is a graph that illustrates extinction and polarization spectra of silver island films compared to silica, according to an embodiment of a substrate.

FIG. 6 is a graph 600 that illustrates extinction and polarization spectra of silver island films (SIFs) compared to silica, according to an embodiment of a substrate. The horizontal axis 602 indicates electromagnetic wave wavelengths in nanometers (nm) of incident polarized light. The left-side vertical axis 604 indicates amount of extinction as measured by the optical density. Optical density is defined by Equation 4.

$$\text{Optical density} = -\log_{10}(I_T/I_0) \quad (4)$$

where $I_0$ is the incident intensity and $I_T$ is the intensity transmitted per unit length of a material. The right-side vertical axis 606 indicates extent of polarization in terms of value of a polarization measure, P. P is directly (but not linearly) proportional to anisotropy, r, as defined above in Equation 2. Polarization, P, is defined by Equation 5.

$$P = (I1 - I2)/(I1 + I2) \quad (5)$$

where I1 and I2 are, as defined above for Equation 2, intensities of parallel and perpendicular electric vectors, respectively, compared to the incident em waves that excite fluorescence.

Trace 610 shows the extinction spectrum for electromagnetic waves transmitted through the quartz substrate with SIF. There is an absorption spectrum maximum near 460 nm (optical density of about 1.25) which is typical for silver particles of sub-wavelength size.

Trace 620 shows the polarization spectrum for electromagnetic waves scattered from the SIFs. The depolarization effect is less than 10% below perfectly polarized backscattered light indicated by P=1.0; varying from P values about 0.97 at 300 nm wavelength to about 0.93 at 500 nm—near the absorption maximum at 460 nm. The polarized incident light results in highly polarized scattered light indicating that the near-field evanescent field from silver island films is radiated into a far-field signal with highly preserved polarization over a broad range of wavelengths that exceed the visible band. The polarization spectrum for a silica substrate without SIF is shown for comparison as trace 630; and is essentially completely polarized (P>0.98) for all wavelengths.

2.1.2 Fluorophores in Solution

The protein streptavidin is known to be easily labeled with a wide range of fluorophores and is suitable for testing the effects of SIF on multiple fluorophores. In addition, streptavidin binds to biotinylated bovine serum albumin (BSA-bt), which can be affixed to a substrate with SIFs. Thus BSA-bt can be used to fix streptavidin and all its fluorophore labels to a substrate in the vicinity of the SIFs to determine the effect of the SIFs on fluorescence polarization. Streptavidin is a large molecule (over 66 kDa) that is not considered suitable as a detection molecule for traditional FPIA. Streptavidin labeled with one or more fluorophores is called a streptavidin-dye conjugate herein.

To determine whether there is a measurable change of fluorescence polarization when bound to SIFs, the fluorescence properties of the streptavidin fluorophores are first determined in solution.

Streptavidin-dye conjugates were acquired from Invitrogen of Carlsbad, Calif. (Alexa Fluor 488-SA, Alexa Fluor 532-SA, Alexa Fluor 635-SA, Alexa Fluor 680-SA), Pierce Biotechnology of Rockford, Ill.; (DY495-SA and DY547-SA), GE Healthcare Life Sciences of Piscataway, N.J. (Cy3-SA and Cy5-SA), and Sigma Aldrich of St. Louis, Mo. (Fluorescein-4-Biotin (Fl-Bt)). Buffer components and other chemicals were also obtained from Sigma-Aldrich.

Figure 4:
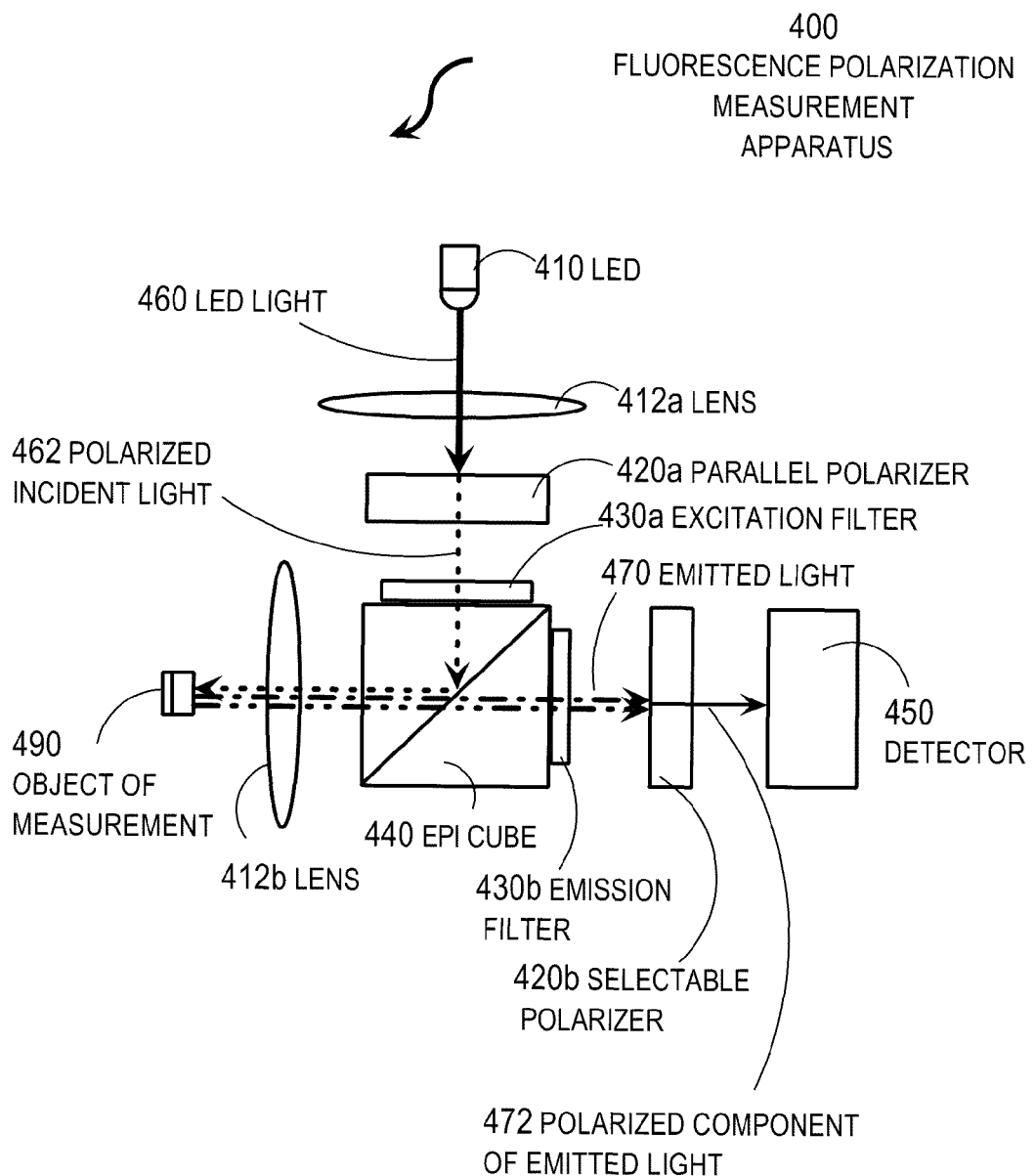
FIG. 4 is a block diagram that illustrates an example polarization anisotropy measurement system, according to an embodiment.

Emission anisotropy measurements were performed using epi-illumination configuration, as depicted in FIG. 4. FIG. 4 is a block diagram that illustrates an example of a polarization anisotropy measurement apparatus 400, according to an embodiment. The apparatus 400 is called a fluorescence polarization measurement apparatus and is suitable for MEF-P affinity assays. Apparatus 400 includes light emitting diode (LED) 410, Lenses 412a and 412b, polarizers 420a and 420b, filters 430a and 430b, Epi cube 440 and detector 450, such as a photo-multiplier tube (PMT) or a charge-coupled device (CCD). Although an object of measurement 490 is depicted in FIG. 4, the object 490 is not part of apparatus 400, but is operated upon by apparatus 400. In some embodiments, the object 490 is a product formed during an assay described below. During the experimental measurements described in this section, object 490 is prepared in accordance with the descriptions in this section. Also depicted in FIG. 4 are light beams produced during operation of the apparatus 400, including LED light 460, linearly polarized incident light 462, emitted light 470 and one polarized component 472 of the emitted light 470.

Light from LED 410 was collimated with lens 412a, linearly polarized in a first direction with Glann-Thompson polarizer 420a, and directed through excitation bandpass filter 430a, dichroic splitter in Epi cube 440, and lens 412b to the object 490. The fluorescent light emitted from the object 490 was passed through lens 412b, Epi cube 440, and emission filter 430b, and collected at detector 450 with one of two orthogonal polarizations determined by selectable polarizer 420b. The two orthogonal polarizations are one parallel and one perpendicular to the excitation polarization direction.

The measured anisotropies were corrected for different detection sensitivities to two orthogonal polarizations using highly depolarized emission of fluorescein in water with expected very low anisotropy of 0.026. The epi-illumination alignment was also verified using a sample with Ludox, a silica suspension in water which is expected to result in polarization degree close to 1.0 (curve 630 in FIG. 6 described above). It was found that the measured polarization of Ludox was about 0.94 which indicates that a high degree of polarization of excitation light has been achieved using LEDs and epi-illumination.

Fluorescence lifetimes were measured using frequency-domain fluorometer (K2 from ISS, Champaign, Ill.). Lifetimes were determined using one- or two-exponential models fit to the observations. These models are represented by Equation 6.

$$I(t) = \Sigma_i \alpha i \exp(-t/\tau i) \qquad (6)$$

where I is intensity at time t, i indicates an ith component of several exponential components, exp is the exponential function in which the base e is raised to the value of the argument inside parentheses, αi is amplitude of the ith component and τi is the lifetime of the ith component at which time the component falls to 1/e of its value at time t=0. The number of components used is increased until a good fit is obtained for the data. Amplitude weighted lifetimes <τ> are defined by Equation 7a.

$$<\tau> = \Sigma_i \alpha i * \tau i \qquad (7a)$$

Intensity weighted lifetimes, $\tau_M$, are defined by Equation 7b.

$$\tau_M = \Sigma_i fi * \tau i \qquad (7b)$$

Where fi is the fractional intensity defined by Equation 7c $$fi = \alpha i * \tau i / \Sigma_i \alpha ti * \tau i \qquad (7c)$$

The LED 410 excitation sources were blue LED (Nichia of York, Pa., NSPB 500S) with maximum at 470 nm and red LED (Nichia NSPR633AS), with maximum at 633 nm. Because of broad tails of LEDs that extend to long wavelengths, bandpass filter 430a was used in the excitation path. LEDs were modulated by applying a RF driving current to the LED in the frequency range from 5-350 MHz. Blue LED was used for excitation of Fluorescein-Bt, Alexa Fluor 488, Alexa Fluor 532, DY495, DY547, and Cy 3 using bandpass excitation filter 430a at 460/40 nm (center wavelength/wavelength bandwidth) and emission filter 430b at 555/50. Red LED was used for excitation of Alexa Fluor 635, Alexa Fluor 647, Alexa Fluor 680, and Cy 5 using excitation bandpass filter 430a at 635/30 nm and long pass emission filter 430b above 667 nm.

The spectroscopic properties of investigated streptavidin-dye conjugates in buffer solution are summarized in the Table 1. Dye to protein ratio (D/P) varied from about 1.0 to 3.9. Higher D/P ratios than 4 usually lead to the self quenching and depolarization effects. The spectral range of used fluorophores span a wide range of wavelengths from about 495 nm to about 675 nm. The extinction coefficient ∈ is a physical property of the conjugate in solution, is expressed in units of inverse Mole centimeters ($M^{-1}$ $cm^{-1}$, where 1 cm=$10^{-2}$ meters) and is akin to an optical cross section for interactions with an incident beam. The wavelengths of maximum absorption ($\lambda_{ABS}$) and the wavelength of maximum emission ($\lambda_{EMS}$) are given in nanometers. Intensity weighted lifetime and amplitude weighted lifetime are given in nanoseconds.

TABLE 1

Spectral properties of streptavidin-daye conjugates in solution

| Dye | D/P | ε | $\lambda_{ABS}/\lambda_{EMS}$ | $\tau_i$ (ns) | $\alpha_i$ | $f_i$ | <τ> | $\tau_M$ |
|---|---|---|---|---|---|---|---|---|
| Fluorescein-Bt | N/A | 68,000 | 494/518 | 4.11 | 1.0 | 1.0 | 4.11 | 4.11 |
| AlexaFluor 488 | 3.9 | 71,000 | 495/519 | 3.08 | 0.4778 | 0.7382 | 1.759 | 2.418 |
|  |  |  |  | 0.55 | 0.5222 | 0.2618 |  |  |
| DY495 | 1.0 | 70,000 | 495/520 | 3.91 | 0.4519 | 0.7991 | 2.211 | 3.287 |
|  |  |  |  | 0.81 | 0.5481 | 0.2009 |  |  |
| AlexaFluor 532 | 4.1 | 81,000 | 529/551 | 2.60 | 0.1530 | 0.4968 | 0.804 | 1.533 |
|  |  |  |  | 0.48 | 0.8470 | 0.5032 |  |  |
| DY547 | 1.0 | 150,000 | 553/572 | 3.76 | 0.0159 | 0.1926 | 0.316 | 0.934 |
|  |  |  |  | 0.26 | 0.9841 | 0.8074 |  |  |
| Cy 3 | 1.7 | 150,000 | 558/578 | 1.23 | 0.3145 | 0.6684 | 0.579 | 0.915 |
|  |  |  |  | 0.28 | 0.6855 | 0.3316 |  |  |
| AlexaFluor 635 | 1.5 | 140,000 | 632/647 | 4.88 | 0.3977 | 0.4681 | 3.995 | 4.037 |
|  |  |  |  | 3.41 | 0.6023 | 0.5139 |  |  |
| AlexaFluor 647 | 2.7 | 239,000 | 653/669 | 2.11 | 0.6260 | 0.4447 | 1.485 | 1.183 |
|  |  |  |  | 0.44 | 0.3740 | 0.5553 |  |  |
| Cy 5 | 0.9 | 250,000 | 657/678 | 1.86 | 1.0 | 1.0 | 1.86 | 1.86 |
| AlexaFluor 680 | 2.8 | 184,000 | 679/675 | 1.98 | 1.0 | 1.0 | 1.98 | 1.98 |

Using a one- or two-exponential component model, the mean fluorescence lifetimes (intensity weighted) for the streptavidin-dye conjugates in solution varied from 4.11 ns (fluorescein-Bt) to 0.93 ns (DY543-SA). Many of these lifetimes are too short to be considered suitable for conventional FPIA. The presence of short lifetime exponential components resulted in amplitude weighted <τ> lifetimes being substantially shorter than intensity weighted lifetimes, $\tau_M$. This is well manifested for DY547-SA and Alexa Fluor 532-SA where the short components contribute significantly in the total emission, with fractional intensities of 0.5032 and 0.8074, respectively. The origin of lifetime heterogeneity of fluorophores when conjugated to proteins can be due to various dye environments, hydrophobicity as well as dye-dye interactions for high D/P ratios.

Fluorescence anisotropies of streptavidin-dye conjugates were first measured in the buffer solution. Due to the large molecular weight of streptavidin, the observed anisotropies are relatively high. One can estimate that the rotational correlation time of streptavidin in the buffer solution, which size is similar to HSA (about 65 kDa), is about 42 ns. The observed fluorescence anisotropy values for probes in solution range from 0.087 to 0.203 (see Table 3, described in more detail below). The literature shows that proteins labeled with multiple fluorophores (Alexa Fluor 488-SA, Alexa Fluor 647-SA, and Alexa Fluor 532-SA) display lower anisotropies because of possible excitation energy transfer (homo-FRET) among multiple fluorophores which causes depolarization of fluorescence. Thus, most of the experiments were carried out on streptavidin labeled with a single fluorophore.

Anisotropy values of streptavidin-dye conjugates were also measured when in the presence of excess biotinylated bovine serum albumin (BSA-bt) in solution and again when BSA-Bt was fixed to a glass surface without SIFs. In these experiments, BSA-bt is analogous to a target molecule in an assay. Binding of the streptavidin conjugates to the BSA-Bt in solution or on glass surface without SIFS resulted in minor changes of anisotropy values (Table 3, below) indicating that the rotational correlation time of the streptavidin itself is sufficiently large compared to the lifetimes of the tested fluorophores.

2.1.2 Fluorophores Fixed to Substrate with SIFs

The surface of SIFs was coated with biotinylated bovine serum albumin (BSA-bt) to provide a mechanism to fix the streptavidin-dye conjugates to the substrate in the vicinity of the SIFs. In these experiments, BSA-bt is analogous to a target molecule. The BSA-bt was electrostatically immobilized on the bare glass and SIFs after incubation in phosphate buffer at pH 7.4 for 1 hour. After washing out unbound BSA-bt, a functionalized substrate was produced. A solution of streptavidin-dye conjugates was incubated for 1 hour in contact with the functionalized substrate. A silicone adhesive with multiple wells, 2.0 mm in depth and 2.5 mm in diameter (Grace Bio-Labs of Bend, Oreg.), was placed on top of the substrate allowing for incubations and measurements for multiple separate samples on the same SIF substrate. For spectroscopic measurements samples were kept in phosphate buffer.

The effect of the SIFs on fluorescence lifetimes and intensity enhancements are summarized in the Table 2. Enhancement E is the ratio of steady state intensity observed when the fluorophore (dye) is fixed to a substrate with SIFs divided by the steady state intensity observed when the dye is fixed to a glass substrate without SIFs. The results summarized in the Table 2 are for fluorophores fixed to a glass and SIFs via binding of streptavidin-fluorophore conjugates to a layer of BSA-Bt immobilized on bare glass and surface with SIFs. The amplitude weighted lifetime <τ> and intensity weighted lifetimes $\tau_M$ are defined above and listed in nanoseconds. Fluorescein-biotin was attached to SIFS through layers of BSA-bt and Avidin.

TABLE 2

Intensity of streptavidin-dye conjugates fixed to SIFS through BSA-bt.

| Dye | E | $\tau_i$ (ns) | $\alpha_i$ | $f_i$ | <τ> | $\tau_M$ |
|---|---|---|---|---|---|---|
| Fluorescein | 6.8 | 2.0 | 0.0335 | 0.3762 | 0.182 | 0.827 |
|  |  | 0.12 | 0.9665 | 0.6238 |  |  |
| AlexaFluor 488 | 7.5 | 1.28 | 0.0361 | 0.2496 | 0.181 | 0.424 |
|  |  | 0.14 | 0.9639 | 0.7504 |  |  |
| DY495 | 9.1 | 1.76 | 0.0336 | 0.3698 | 0.157 | 0.714 |
|  |  | 0.10 | 0.9664 | 0.6302 |  |  |
| AlexaFluor 532 | 11.2 | 2.25 | 0.0096 | 0.1451 | 0.140 | 0.429 |
|  |  | 0.12 | 0.9914 | 0.8549 |  |  |
| DY547 | 14.2 | 0.87 | 0.0155 | 0.2355 | 0.052 | 0.235 |
|  |  | 0.04 | 0.9845 | 0.7645 |  |  |
| Cy 3 | 9.8 | 2.06 | 0.0106 | 0.1763 | 0.120 | 0.446 |
|  |  | 0.10 | 0.9804 | 0.8237 |  |  |
| AlexaFluor 635 | 12.4 | 2.19 | 0.0378 | 0.3259 | 0.256 | 0.835 |

TABLE 2-continued

Intensity of streptavidin-dye conjugates fixed to SIFS through BSA-bt.

| Dye | E | $\tau_i$ (ns) | $\alpha_i$ | $f_i$ | $\langle\tau\rangle$ | $\tau_M$ |
|---|---|---|---|---|---|---|
|  |  | 0.18 | 0.9622 | 0.6741 |  |  |
| AlexaFluor 647 | 8.1 | 1.19 | 0.0486 | 0.2593 | 0.220 | 0.434 |
|  |  | 0.17 | 0.9514 | 0.7407 |  |  |
| Cy 5 | 9.0 | 2.02 | 0.0333 | 0.3034 | 0.222 | 0.724 |
|  |  | 0.16 | 0.9667 | 0.6966 |  |  |
| AlexaFluor 680 | 14.1 | 2.02 | 0.0318 | 0.2736 | 0.267 | 0.705 |
|  |  | 0.21 | 0.9682 | 0.7264 |  |  |

The fluorescence intensity and the fluorescence decay constants are strongly enhanced in the presence of silver island films. The enhancement (E) factor varies from 6.8 for fluorescein-biotin to 14.2 for DY547-SA.

Intensity decays were fit to a two exponential model resulting in very short component of 40 to 200 picoseconds (ps, 1 ps=$10^{-12}$ seconds=$10^{-3}$ nanoseconds) for most dyes. This short lifetime component is attributed to the strong fluorophores-plasmon interactions. The longer lifetime components are likely representative of the fluorophores that weakly interact with plasmons or fluorophores located on the glass. Due to very large differences between decay components, two average lifetimes (amplitude and intensity weighted) differ substantially. It is observed that the amplitude weighted lifetime decreased approximately 10-fold for most fluorophores (compare Table 1 and Table 2). The intensity-weighted lifetimes did not decrease as much because they are dominated by the long lifetime component. Representative frequency-domain intensity decays for fluorescein-biotin and DY547-SA are shown in FIG. 5A and FIG. 5B, respectively.

FIG. 5A is a graph that illustrates examples of intensity decays for a Fluorescein fluorophore, both in solution and bound to a functionalized substrate, according to an embodiment. The horizontal axis 502 is sampling frequency in megahertz (MHz, 1 MHz=$10^6$ Hertz, where 1 Hertz, Hz, =1 sample per second). The left-side vertical axis 504 is phase angle in degrees of the measured fluorescent emissions. The right-side vertical axis 506 is amplitude modulation of the measured fluorescent emissions. Curve 510 shows the measured phase of fluorescent emissions from streptavidin-Fluorescein-biotin conjugates free in solution. Curve 530 shows the measured phase of fluorescent emissions from Fluorescein-biotin conjugates bound to streptavadin fixed to the SIFs via a layer of BSA-bt. Curve 520 shows the measured amplitude modulation of fluorescent emissions from Fluorescein-biotin conjugates free in solution. Curve 540 shows the measured amplitude modulation of fluorescent emissions from Fluorescein-biotin conjugates bound to streptavadin fixed to the SIFs via a layer of BSA-bt.

The phase and modulation of the fluorescence are directly related to the fluorescence lifetime, which for single exponential decay is described by Equation 8a and Equation 8b.

$$\phi = \tan^{-1}(\omega\tau) \quad (8a)$$

$$m = (1+\omega^2\tau^2)^{-1/2} \quad (8b)$$

where $\phi$ is phase in degrees, $\omega$ is modulation angular frequency ($\omega=2\pi f$, where f is the frequency in Hertz), $\tau$ is the fluorescence lifetime, and m is fluorescence modulation. The phase shift and modulation of the fluorescence are measured relative to the em waves used to excite fluorescence. The results presented in FIG. 5A show that fluorescein-biotin when bound to the bioactive layer display substantially decreased lifetime; indicated by decreased values of phase trace 530 and increased values of modulation trace 540 relative to the values in trace 510 and trace 520, respectively, for fluorescein in solution FIG. 5B is a graph that illustrates examples of intensity decays for a DY547-SA conjugate, both in solution and bound to a metal film functionalized substrate, according to an embodiment. The axes 502, 504 and 506 are as described above for FIG. 5A. Curve 560 shows the measured phase of fluorescent emissions from streptavidin-DY547-SA conjugates free in solution. Curve 580 shows the measured phase of fluorescent emissions from streptavidin-DY547 conjugates fixed to the SIFs. Curve 570 shows the measured amplitude modulation of fluorescent emissions from streptavidin-DY547 conjugates free in solution. Curve 580 shows the measured amplitude modulation of fluorescent emissions from streptavidin-DY547 conjugates bound to BSA-bt fixed to the SIFs. The results presented in FIG. 5B demonstrate the short lifetime fluorophore DY547 which is an excellent fluorophore for MEF-P bioassay applications but not useful for standard FPIAs because of short lifetime.

The observed fluorescence anisotropy, r, values for probes in solution and fixed to substrates with and without the SIFS are shown in Table 3. The values for the streptavidin-dye conjugates free in solution are listed in the column labeled "Free." The values for the conjugates bound to BSA-bt in solution are listed in the column labeled "Bound to BSA-Bt." The values for the conjugates bound to BSA-bt on glass without SIFS are listed in the column labeled "Bound to BSA-Bt on glass." The values for the conjugates bound to BSA-bt affixed to the SIFs are listed in the column labeled "Bound to BSA-Bt on SIFs."

TABLE 3

Emission anisotropy values of streptavidin-dye conjugates in various environments.

| Dye | Free | Bound to BSA-Bt | Bound to BSA-Bt on Glass | Bound to BSA-Bt on SIFs |
|---|---|---|---|---|
| Fluorescein-bt | 0.021 | 0.194 | 0.191 | 0.038 |
| AlexaFluor 488 | 0.087 | 0.088 | 0.087 | 0.036 |
| DY495 | 0.129 | 0.150 | 0.127 | 0.035 |
| AlexaFluor 532 | 0.139 | 0.128 | 0.094 | 0.035 |
| DY547 | 0.203 | 0.202 | 0.109 | 0.034 |
| Cy 3 | 0.146 | 0.137 | 0.112 | 0.037 |
| AlexaFluor 635 | 0.143 | 0.148 | 0.067 | 0.062 |
| AlexaFluor 647 | 0.087 | 0.094 | 0.069 | 0.061 |
| Cy 5 | 0.134 | 0.160 | 0.098 | 0.057 |
| AlexaFluor 680 | 0.125 | 0.174 | 0.106 | 0.042 |

In contrast to the conjugates in solution and bound to glass, the anisotropy values dramatically decreased when probes were bound to the SIF surface. This is a somewhat unexpected observation because one would expect, a priori, an increase in anisotropy due to the substantially reduced fluorescence lifetime and limited rotational motion upon binding to the SIFs compared to rotational motion allowed in solution. Surprisingly, while the lifetime of bound probes decreased several-fold and rotational motions were decreased upon binding to the SIFs, the fluorescence polarization decreased from 3 to 5-fold. The observed decreased polarizations were larger for fluorophores excited in the blue wavelength range than in the red.

There are probably several reasons for the strong depolarization, which are discussed below. The following discussion is provided as a theoretical framework for the purposes of understanding this embodiment. However, embodiments of the invention are not limited by the correctness or accuracy of this theoretical discussion.

Highly depolarized emissions in presence of SIFs cannot be explained only by the depolarization effects of scattered excitation light, as demonstrated by the still high polarization values of curve 620 in FIG. 6, described above. The inventors believe that the random distribution of silver nanoparticles of various sizes and shapes in SIFs, which display a broad wavelength band (e.g., the extinction spectrum 610 in FIG. 6), can support multi-mode surface plasmons that can be excited by fluorophores in excited states.

There are several possible origins for the depolarized fluorescence. While the incident light is highly polarized, it is likely that the polarization of the effective excitation field is far less polarized. This can be understood by imagining a fluorophore dipole in the incident-light induced field around a metal particle. The field lines have to change from vertical polarization on the sides of the metal particle to horizontal at the top of the particle, and then curve back into the particle. Hence, the angular distribution of the excited fluorophores will be less polarized in the presence of silver particles then with plane wave excitation. Additionally, with regard to emission, the fluorophores undergo near-field interactions with the metallic particles, which results in a more complex field distribution around the particle than is induced by far-field planar wave illumination. Hence, the plasmon-coupled emission will display a higher degree of depolarization than is observed from the polarization of the far-field scattered incident light.

Therefore, the observed depolarization of emission can be due to strong interaction between excited fluorophores and plasmon resonance on the surface of the silver particles, which leads to loss of the anisotropy observed from the fluorophore alone. The multiple radiating systems consisting of excited fluorophores and silver particles radiate randomly as observed by the depolarized far field signal that is measured by apparatus 400. This means that an exchange of excitation energy between fluorophore and particle plasmon leads to a depolarization effect. At first glance this result may seem similar to the homo-transfer between two identical fluorophores where energy migration always results in depolarization of emission. Our sample of Alexa Fluor 488-SA is such an example where four fluorophores are attached to one streptavidin molecule with already partially depolarized emission compared to very similar DY495-SA that has one fluorophore per streptavidin (Table 2). However, the analogy is not perfect because of the increased complexity of fluorophore-metal-plasmon interactions.

The short lifetime accompanied with large intensity enhancement observed for each fluorophore indicate that strong coupling between excited fluorophores and particle plasmon occurs.

Furthermore, the local depolarization of the affected molecule due to SIFs is likely even higher than the observed composite values in the far field measured by apparatus 400. This is because there is a fraction of fluorophores that do not interact (or interact weakly) with particle plasmon and thus increase the observed anisotropy. An estimation can be performed using additive properties of emission anisotropy, as expressed in Equation 9.

$$r(\text{observed}) = f_1 * r_1 + f_2 * r_2 \qquad (9)$$

where the r(observed) is observed anisotropy, the $r_1$ and $r_2$ are anisotropies associated with short and long lifetime component, respectively, and the $f_1$ and $f_2$ are fractional intensities of short and long lifetime components ($f_1+f_2=1$), respectively, as described above. Using the values in Table 2, one can estimate that the contribution of the long lifetime component accounts approximately for 40 to 60% of the measured anisotropy on the SIFs. For example, for Alexa Fluor 532, the fractional intensity of the long component, $f_1=0.1451$, which multiplied by $r_1=0.094$ (anisotropy on glass, Table 3) results in 0.014 which is 40% of the measured r value of 0.035.

2.1.3 Potential for MEF-P Assays

The observed depolarized MEF-P emissions have promising advantages for design of polarization based affinity assays, such as immunoassays, and studies of interactions between biomolecules.

None of the streptavidin-dye conjugates can be regarded as conventional polarization probes because they do not display a useful change in anisotropy values when they bind to the biotinylated BSA in solution (see Table 3). This is because the molecular weight of streptavidin of about 66 kDa results in a long rotational correlation time that can be estimated at about 40 ns in aqueous solution.

In contrast, all streptavidin-dye conjugates can be regarded as excellent polarization detection molecules for biotinylated proteins when binding occurs on a substrate with metal nanoparticles, which supports fluorophore-plasmon interaction. The mechanism for depolarization is not due to change in molecular weight due to binding (or dissociation) but the localized space where the bimolecular interaction and the complex near-field plasmon interactions occur.

Simulations are used here to show that a fluorophore labeled large biomolecule can be used as a detection molecule for the design of MEF-P FPIA where the binding occurs on the surface of the MEF substrate. The binding event places the fluorophore in proximity to metallic particles where the fluorophore-plasmon interactions cause depolarization of fluorescent emissions. Equation 1 and Equation 3 for rotating molecules do not apply to MEF-P assays where the detection molecule is bound to the functionalized substrate.

Figure 7:
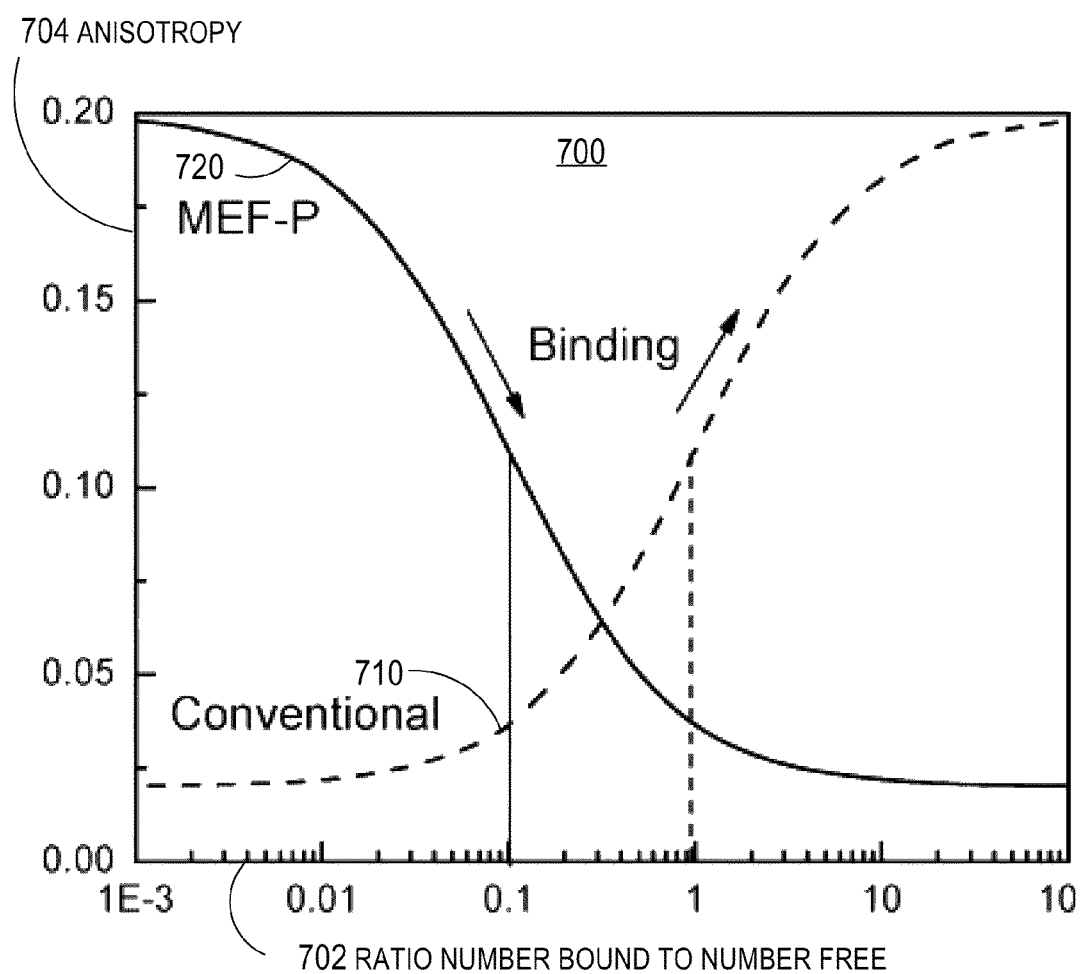
FIG. 7 is a graph that illustrates an example curve for converting measured anisotropy to a ratio of free to bound fluorophores in an assay, according to an embodiment.

FIG. 7 shows simulated results of a MEF-P assay. FIG. 7 is a graph 700 that illustrates an example curve relating measured anisotropy to a ratio of free to bound fluorophores in an assay, according to an embodiment. Horizontal axis 702 indicates a ratio of a number of bound detection molecules to a number of free detection molecules. The vertical axis indicates the degree of polarization, as quantified by an anisotropy, r, value. Curve 710 is an example curve for a conventional FPIA. The anisotropy increases with increase of the number of bound probes relative to the free probes. When there are few bound detection molecules, the anisotropy is low indicating that parallel and perpendicular components are about equal. The emissions can not said to be polarized. As more detection molecules bind to the larger target molecule in solution, the anisotropy increases. At saturation where the curve 710 flattens to the upper right of the graph 700, the number of bound detection molecules is high and the measured anisotropy r value is high. The number of unlabeled analytes present in the test sample must be low. There is usually no change in intensity of the fluorophore emissions upon binding to the bioactive layer.

Curve 720 is an example curve for MEF-P competitive binding assay. When there are few bound detection molecules, the anisotropy, r, value is moderate because the detection molecule (such as streptavidin-dye conjugate) is large or the fluorescence lifetime ($\tau$) of the fluorophore is short, or both. For example, the free detection molecule displays anisotropy of 0.2. When the detection molecules predominate the binding to the MEF-P substrate, the intensity is enhanced 10-fold and emission is depolarized to an anisotropy value of 0.02. Because of the increased intensity upon binding for MEF-P assays, the method is more sensitive even with small numbers of bound detection molecules.

Assuming for purposes of illustration that fractional intensities are proportional to the number of respective molecules, one can rewrite Equation 9 and express relation between molar ratio of bound to free probes ($N_B/N_F$) with the observed anisotropy (r) as shown in Equation 10.

$$\frac{N_B}{N_F} = \frac{r - r_F}{r_B - r} \frac{1}{E} \quad (10)$$

where the $r_F$ and $r_B$ are the anisotropy values of free and bound probes, respectively, and E is the intensity enhancement of the probe upon binding, as listed in Table 2. In the standard FPIAs the factor E is usually close to 1.0 (detection molecule does not change intensity upon binding) however in the case of MEF-P, the E factor is much larger than 1.0 as shown in Table 2.

2.2 Functionalized Substrate

According to some embodiments of the invention a functionalized substrate is provided for MEF-P affinity assays.

FIG. 2A is a block diagram that illustrates an example of a functionalized substrate 200 for a metal enhanced fluorescence polarization (MEF-P), according to an embodiment. The functionalized substrate 200 includes a glass substrate 210, with several wells 212 that are used for separating reactions. Deposited in the wells is a film of metal nanoparticles 220. Deposited on the film of metal nanoparticles is a layer of bioactive molecules. In some embodiments, there are no wells and the entire glass substrate is coated uniformly with a film of metal nanoparticles 220 and layer of fixed bioactive molecules 230.

Any material which does not unduly interact with test samples, analytes, detection molecules or target molecules may be used as a substrate. For example glass, quartz and plastic are used as substrate in some embodiments. Substrates can be organic or inorganic.

Any noble metal may be deposited. In various embodiments, the film of metal nanoparticles 220 is one or more silver island films (SIFs) deposited as described above or films of one or more other metal nanoparticles such as gold, copper and aluminum.

Any method may be used to deposit the film of metal nanoparticles 220. For example, the metal nanoparticles may be deposited using a wet chemical deposition method as described above to coat the substrate 210 with the SIFs. In other embodiments, other methods are used to deposit the metal nanoparticles, such as thermal vapor deposition or deposition by sputtering, or patterning using electron beam lithography.

Any distribution of nanoparticle sizes may be deposited. In a preferred embodiment, the nanoparticle sizes include a large number in a size range that is small compared to the wavelengths of fluorescent emissions from a particular fluorophore or a particular set of one or more fluorophores to be used with the substrate. In an example embodiment, the nanoparticles are deposited in a dense configuration to reduce the area of voids where MEF-P does not occur. The void dimensions are preferably small compared to a maximum distance for effective MEF-P, such as 50 nm or less.

Any molecule may be deposited in the bioactive molecule layer 230. The properties of the functionalized substrate are affected by the bioactive molecule deposited in layer 230. The molecule should include a functional group to affix the molecule to the substrate or metal film, such as a ligand to affix the molecule to a metal nanoparticle. The molecule should also be able to bind to a particular analyte of interest. Such a molecule is also called a target molecule for an assay for the analyte. In illustrated embodiments, all the molecules deposited in the layer 230 are substantively identical. In various embodiments, target molecules that are deposited in the layer 230 include, but are not limited to, a polymer, a ligand, an antigen, an antibody, a protein, a peptide, DNA, RNA, or an oligonucleotide.

Any analyte may bind to a target molecule included the bioactive molecule. In various embodiments, the analyte includes, but is not limited to, a polymer, a ligand, an antigen, an antibody, a protein, a peptide, DNA, RNA, oligonucleotide, a virus or a bacterium.

Figure 2B:
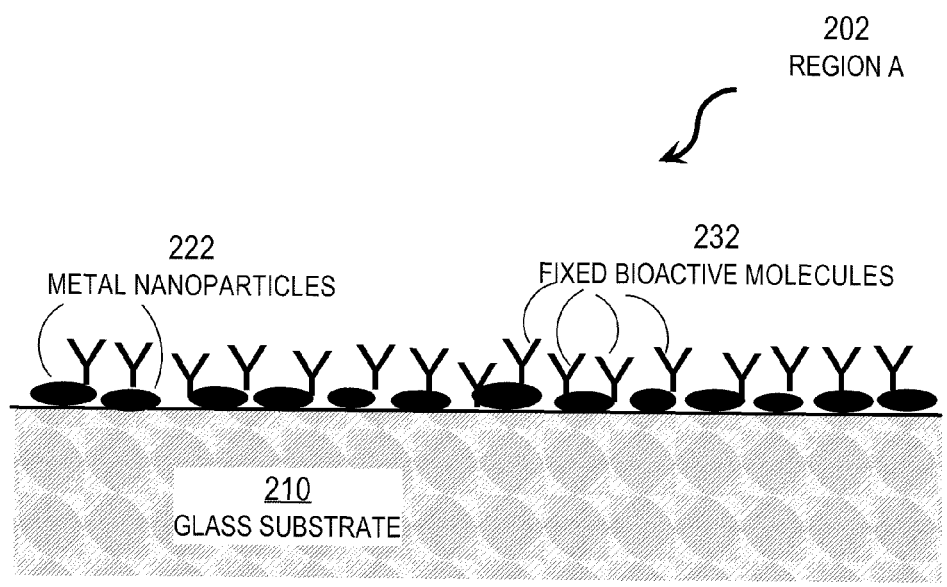
FIG. 2B is a block diagram that illustrates an example portion of the functionalized substrate of FIG. 2A, according to an embodiment.

Region A 202 in a well 212 of the functionalized substrate 200 is indicated in FIG. 2A as an example portion of the substrate 210, film 220 and layer 230. FIG. 2B is a block diagram that illustrates an example portion 202 of the functionalized substrate of FIG. 2A, according to an embodiment. FIG. 2B depicts the glass substrate 210 and individual metal nanoparticles 222 in the film 220, which are deposited on the glass substrate. The metal nanoparticles vary somewhat in size and separation. FIG. 2B also depicts individual bioactive molecules 232 that are fixed to the substrate, either directly to the glass substrate 210 or directly to the metal nanoparticles 222. The fixed bioactive molecules 232 vary somewhat in their proximity to the individual metal nanoparticles 222. The depicted bioactive molecules 232 are similar in size to the metal nanoparticles. In a preferred embodiment, analyte binding sites on the fixed bioactive molecules 232 are within 50 nm of the surface of a metal nanoparticle 222.

2.3 MEF-P Competitive Binding Assay

In some embodiments, the functionalized substrate 200 is used in a MEF-P competitive binding assay. FIG. 3A is a block diagram that illustrates an example MEF-P competitive binding assay 300 during operation, according to an embodiment. FIG. 3A depicts a portion of a functionalized substrate, as depicted in FIG. 2B, including the glass substrate 210 and metal nanoparticles 222. The functionalized substrate of FIG. 3A also includes fixed target molecules 332 for a particular analyte as the fixed bioactive molecules 232 of FIG. 2B.

The functionalized substrate is in contact with a covering solution 310. The covering solution 310 is a mixture of a test sample and a detection molecule reagent. The test sample includes analyte molecules 320 that do not contain a fluorophore. The reagent includes detection molecules comprising analyte molecules 320 labeled with a fluorophore 330. In other embodiments the detection molecule comprises a fluorophore and a molecule that is different from the analyte, but competes with the analyte for binding sites on the target molecules 332.

As shown in FIG. 3A, the labeled and unlabeled analyte molecules 320 compete for binding sites on the fixed target molecules 332, and eventually reach a steady state equilibrium. The combination of the functionalized substrate and covering solution in steady state is called a product of the assay.

The product of the assay is exposed to polarized electromagnetic waves at a specific wavelength that excites fluorescence of the fluorophore 330. These waves linearly polarized. In the illustrated example, the functionalized substrate and covering solution are exposed to linearly polarized incident light 340 indicated by dotted arrows.

The labeled analyte molecules are excited by the incident light and fluoresce, emitting light at a different specific wavelength. The fluorophore labels on analyte molecules that are free in cover solution 310 emit electromagnetic waves with a particular anisotropy value. For example, a labeled analyte in solution emits solution emitted light 342 indicated by a single dot dash arrow. A collection of the solution emitted light 342 has moderate anisotropy value due to large molecular weight of analyte or short fluorophore lifetime or both. In contrast, the fluorophore labels on analyte molecules that are bound to fixed target molecules 332 emit electromagnetic waves with a much lower anisotropy value due to MEF-P. For example, a labeled analyte bound to fixed target molecules 332 emits film emitted light 344 indicated by a double dot dash arrow. The collection of these emissions has an anisotropy value substantially less than the anisotropy value of a collection of the solution emitted light 342.

The anisotropy of the mixed emitted light is measured using an apparatus like apparatus 400 depicted in FIG. 4. The object 490 is the product of the assay, i.e., the functionalized substrate contacting the covering solution 310. A curve like curve 720 in FIG. 7 can be used to determine the ratio of bound to free labeled analytes for a measured anisotropy value. Other calibration curves, as is well known in the art, are used to determine a resulting analyte associated with such a ratio of bound to free labeled analyte. The resulting analyte is used to determine the quantity (e.g., the presence, absence or concentration) of analyte in the test sample.

2.4 MEF-P Sandwich Binding Assay

In some embodiments, the functionalized substrate 200 is used in a MEF-P sandwich binding assay. FIG. 3B is a block diagram that illustrates an example MEF-P sandwich binding assay 350 during operation, according to an embodiment. FIG. 3B depicts a portion of a functionalized substrate, as depicted in FIG. 2B, including the glass substrate 210 and metal nanoparticles 222. The functionalized substrate of FIG. 3B also includes fixed target molecules 332 for a particular analyte as the fixed bioactive molecules 232 of FIG. 2B.

The functionalized substrate is in contact with a covering solution 360. The covering solution 360 is a result of a three step process.

First the functionalized substrate is contacted to a test sample that includes analyte molecules 370 that are not labeled with a fluorophore. The contact is maintained for sufficient time under conditions that allow the amount of analyte binding to the fixed target molecules 332 to be proportional to the amount of analyte in the test sample. Such times and conditions are easily determined by routine experimentation.

Next, the functionalized substrate is washed to remove excess unbound analyte from the test sample.

Then the functionalized substrate with bound analyte is contacted to a solution of reagent. The reagent includes detection molecules 372. Each detection molecule 370 includes a fluorophore 380 and a molecule that binds to the analyte 370 at a site on the analyte different from the site that binds the analyte to the fixed target molecule 332. The combination of the functionalized substrata, sandwiched analyte and covering solution in steady state is called a product of the assay.

The product of the assay is exposed to linearly polarized electromagnetic waves at a specific wavelength that excites fluorescence of the fluorophore 380. In the illustrated example, the functionalized substrate and covering solution are exposed to polarized incident light 390 indicated by dotted arrows.

The fluorophores in the detection molecules are excited by the incident light and fluoresce, emitting light at a different specific wavelength. The fluorophores on detection molecules that are free in cover solution 360 emit electromagnetic waves with a particular anisotropy value. For example, a detection molecule in solution emits solution emitted light 392 indicated by a single dot dash arrow. The collection of these emissions has a moderate anisotropy value which is associated with the particular detection molecule. In contrast, the fluorophores on detection molecules that are bound to the analyte that is in turn bound to the fixed target molecules 332 emit electromagnetic waves with a much lower anisotropy value due to MEF-P. For example, detection molecules bound to analytes bound to fixed target molecules 332 emit film emitted light 394 indicated by a double dot dash arrow. The collection of these emissions has an anisotropy value substantially less than the anisotropy value of a collection of the solution emitted light 392.

The anisotropy of the mixed emitted light is measured using an apparatus like apparatus 400 depicted in FIG. 4. The object 490 is the product of the assay, i.e., the functionalized substrate contacting the covering solution 360. A curve like curve 720 in FIG. 7 can be used to determine the ratio of bound to free detection molecules for a measured anisotropy value. Other calibration curves, as is well known in the art, are used to determine a resulting analyte associated with such a ratio of bound to free detection molecules. The resulting analyte is used to determine the quantity (e.g., the presence, absence or concentration) of analyte in the test sample.

2.5 Generalized MEF-P Assay

Figure 8:
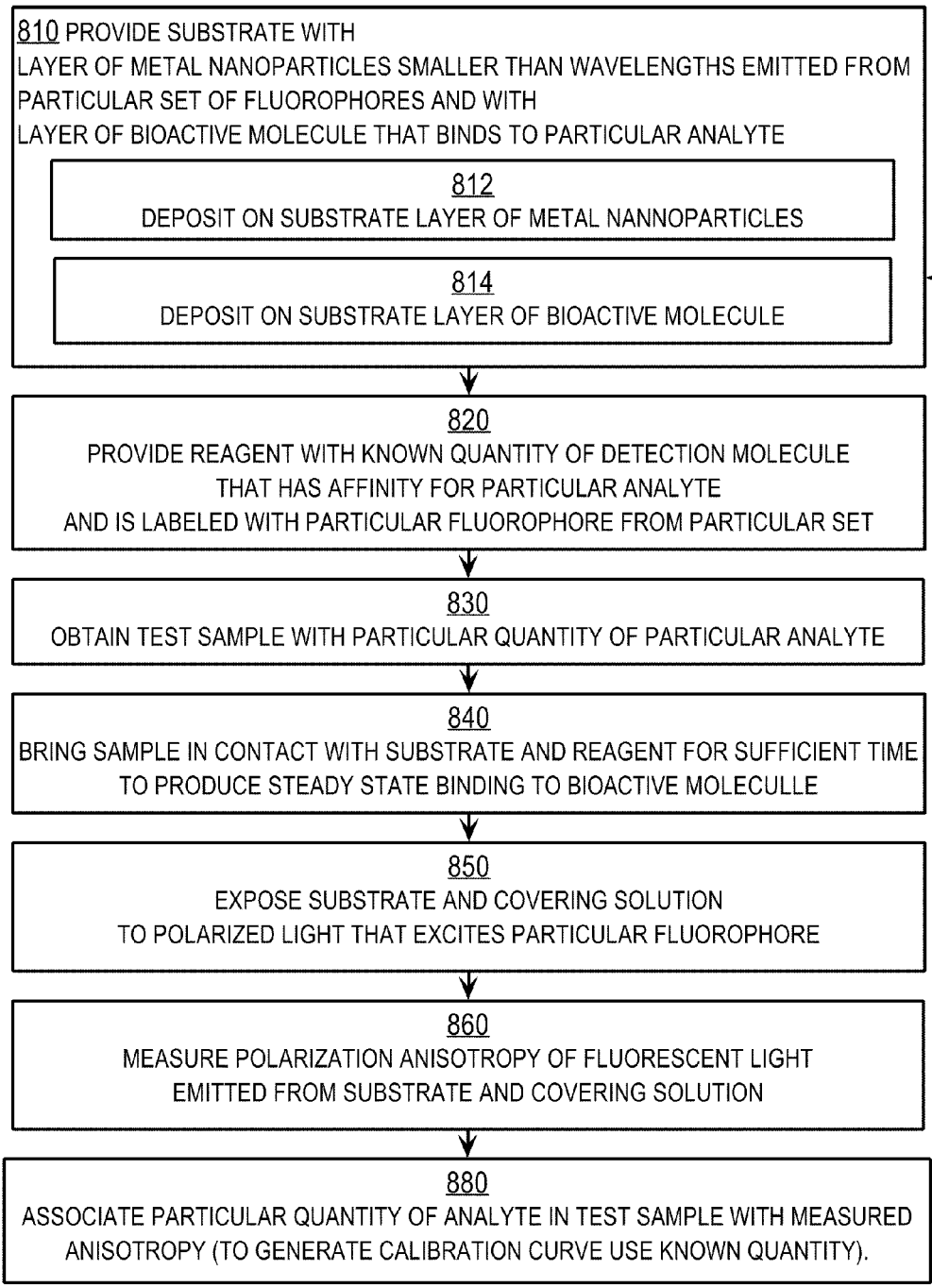
FIG. 8 is a flow diagram that illustrates an example method to make and use MEF-P assays to determine the concentration of an analyte, according to an embodiment.

FIG. 8 is a flow diagram that illustrates an example method to make and use MEF-P assays to determine the presence or concentration of an analyte, according to an embodiment. Although steps are shown in a particular order for purposes of illustration, in other embodiments one or more steps may be performed in a different order or overlapping in time, in series or in parallel, or one or more steps may be omitted, or other steps added, or steps may be changed in any combination of ways.

In step 810, a functionalized substrate is provided. In an illustrated embodiment, the functionalized substrate includes a layer of metal nanoparticles that are smaller than wavelengths emitted from a particular set of one or more fluorophores to be used in an assay. In this embodiment, the functionalized substrate also includes a layer of multiple substantively identical bioactive molecules that bind to a particular analyte of interest.

The functionalized substrate can be provided in any manner. For example, in some embodiments, the substrate is obtained (e.g., from a commercial supplier) with both the metal nanoparticles and layer of bioactive molecule. In some embodiments, the substrate is obtained with the metal nanoparticles already deposited but without the bioactive layer, and the bioactive layer is deposited during step 814. In some of these embodiments the bioactive molecule is supplied and shipped in a separate container (e.g., to preserve its efficacy) as part of an assay kit, and deposited during step 814 to form the functionalized substrate when needed. In some other embodiments, the substrate is obtained with neither the metal nanoparticles nor the bioactive layer. In such embodiments, the metal nanoparticles are deposited during step 812, and the bioactive molecule layer is deposited during step 814.

Any metal may used in the metal nanoparticles, such as gold, silver, copper and aluminum. Any molecule may serve as the target molecule in the bioactive layer, such as a polymer, a ligand, an antigen, an antibody, a protein, a peptide, DNA, RNA, or an oligonucleotide.

In step 820, a reagent is provided, typically in solution. The solution of reagent includes a known quantity of a detection molecule comprising a probe and a fluorophore. The probe is selected to assay for the particular analyte. The probe is labeled with a particular fluorophore from the particular set of fluorophores with emission wavelengths suitable for plasmon light interactions. The reagent can be provided in any manner. For example, in some embodiments, the reagent is obtained from a commercial supplier. In some embodiments, the reagent is provided in an assay kit that also includes the substrate that has the metal nanoparticles already deposited and the bioactive molecule in a separate container. In some embodiments the reagent is prepared locally by a user of the assay.

Any molecule may be included as the probe in the detection molecule, such as a polymer, a ligand, an antigen, an antibody, a protein, an oligomer, a protein, a peptide, DNA, RNA or an oligonucleotide. Any fluorophore may be included in the detection molecule, such as fluoresceins, eosin, coumarines, rhodamines, cyanines, benzophenoxazines, phycobiliproteins or fluorescent proteins.

In step 830 a test sample is obtained with a quantity of a particular analyte to be determined by the assay. During a calibration phase used in some embodiments, step 830 includes providing a control sample with a known quantity of the particular analyte. For assays that are previously developed, with a known calibration curve, a control sample is not used during step 830. The quantity (such as the presence or concentration) of the analyte in the test sample is determined during step 880, described below. Any material may serve as the analyte, such as a polymer, a ligand, an antigen, an antibody, a protein, a peptide, DNA, RNA, oligonucleotide, a virus or a bacterium.

In step 840, the functionalized substrate is contacted with the test sample and the reagent for sufficient time to produce steady state binding to the bioactive molecule. For example, when the method 800 is for a competitive binding assay, the functionalized substrate is brought into contact with a mixture of the test sample and the reagent. The mixture is allowed to remain in contact with the functionalized substrate for sufficient time and under conditions that allow the analyte and detection molecules to bind to the target molecules fixed to the substrate. When the method 800 is for a sandwich binding assay, the functionalized substrate is brought into contact with the test sample first and allowed to remain in contact for sufficient time to allow the analyte to bind to the target molecules fixed to the substrate in amounts that are proportional to the amount of analyte in the test sample. The functionalized substrate with bound analyte is then washed to remove excess analyte. Then the functionalized substrate with bound analyte is contacted with the solution of the reagent. This contact is maintained for sufficient time to allow the detection molecule to bind to the analyte fixed by the target molecule to the functionalized substrate.

In step 850, the substrate and covering solution resulting from step 840 are exposed to polarized electromagnetic waves, such as light, that excites fluorescence in the particular fluorophore.

In step 860 the angular dependence of electromagnetic wave polarization, called polarization anisotropy, is measured. Any measure may be used. In the illustrated embodiments, one or both of the polarization measure P or anisotropy measure r of the fluorescent light emitted from the substrate and covering solution is measured. In the illustrated embodiment, step 860 overlaps in time step 850, as the substrate and covering solution are excited and fluoresce in steady state. In the illustrated embodiment, the anisotropy measurement includes taking a first intensity measurement with the selectable polarizer 420b oriented to pass electromagnetic waves parallel to the polarized electromagnetic waves incident on the substrate and covering solution. Step 860 then includes taking a second intensity measurement with the selectable polarizer 420b oriented to pass electromagnetic waves perpendicular to the polarized electromagnetic waves incident on the substrate and covering solution. The two measurements are used to determine an anisotropy value according to Equation 2.

In step 880, a particular quantity of analyte in the test sample is associated with the measured value of anisotropy. During a calibration phase, the known quantity of analyte in the control sample is associated with the measured anisotropy to add a point to the calibration curve. The method then returns to step 810 or step 820 to do another measurement with another known quantity of analyte in another control sample to produce another point for the calibration curve. In a post calibration operational phase, a quantity on the established calibration curve associated with the measured anisotropy is determined to be the quantity of the analyte in the test sample. The quantity indicates, for example, the presence, absence or concentration of the analyte. In some embodiments, the method returns to step 810 or step 820 to do another measurement with another test sample to determine another quantity of analyte in another test sample.

Because the change in polarization of metal enhanced fluorescence (MEF-P) is not due to changes in molecular volume of the bound complex there are several advantages of MEF-P for applications to molecular sensing. (1) Because most fluorophores interact with metal particles the MEF-P assay can be performed with any fluorophore. The suitability of MEF-P is not limited by the lifetime of the fluorophore. (2) Large biomolecules can be labeled with fluorophores as detection molecules because the changes in polarization are due to the binding event, and not to a change in rotational diffusion. The detection molecules can be large antibodies that bind to small unlabeled antigens. A large change in molecular volume after binding is not required for MEF-P assays. (3) The sensitivity of MEF-P is many-fold better than traditional FP assays because the bound detection molecules display enhanced intensity compared to the unbound detection molecules. This means that a small fraction of bound detection molecules generate large changes in anisotropy. FIG. 7 shows that sensitivity of MEF-P is enhanced proportionally to the enhanced intensity (10-fold in the illustrated embodiment). (4) High signal-to-noise ratio in polarization measurements are obtained because of a large change in polarization which affords a large dynamic range.

These advantages substantially broaden and increase sensitivity compared to traditional FPIA applications. The typical calibration curve for conventional FPIA needs a low anisotropy probe which is restricted to fluorescein and low molecular weight biomolecules. In contrast, the MEF-P based assay allows large molecular weight detection molecules (with large in-solution anisotropy) and short lived fluorophores. There are many such fluorophores and biomolecules. For all these choices, the complex bound on the MEF-P substrate will exhibit highly depolarized emission due to plasmon-fluorophore interaction. The sensitivity of MEF-P based assays are expected to be significantly improved because of enhanced emission of bound probes. In addition, the MEF-P assays will require very small quantities of biochemicals in the fixed bioactive layer because the receptor concentration is defined by surface density to which labeled ligand will bind (or dissociate).

3. MEF-P Assay Kit

Some embodiments of the invention are directed to an MEF-P assay kit. In these embodiments, the user is a recipient of the kit. In one embodiment, this kit includes a substrate with a layer of metal nanoparticles and one or more containers of target molecules in solution to functionalize the substrate for assays for one or more corresponding analytes. In some embodiments, the kit also includes one or more containers of detection molecules for the one or more corresponding analytes. In some embodiments, the kit includes containers of unlabeled biomolecules to serve as probes for detection molecules for the one or more corresponding analytes, and containers for one or more fluorophores. Recall that a detection molecule includes a probe and a fluorophore. The fluorophores are selected from a particular set for which emission wavelengths are long compared to the nanoparticle sizes on the substrate. The user labels the biomolecules with a fluorophore chosen from an included container to produce a reagent of detection molecules. In a preferred embodiment, the probe molecules are already labeled with the selected fluorophore and provided in a container as a reagent of detection molecules. In some embodiments, one or more control samples with known quantities of analyte are also included to be used to generate calibration curves. In some embodiments, printed media or a computer-readable medium is included with data that indicates a calibration curve.

The MEF-P assay kit provides the recipient with materials to perform an MEF-P assay on the recipient's own one or more test samples according to one or more embodiments of method 800.

4. Extensions and Modifications

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method for determining the quantity of an analyte comprising:
   a) providing a functionalized substrate that comprises metallic nanoparticles and a plurality of substantively identical bioactive target molecules affixed to a substrate, wherein the bioactive target molecule binds to a particular analyte;
   b) providing a reagent comprising a plurality of substantively identical detection molecules, wherein the detection molecule comprises a fluorophore, and the detection molecule binds to the particular analyte or competes with the particular analyte for binding to the target molecule;
   c) contacting the functionalized substrate to a test sample and the reagent;
   d) exposing the functionalized substrate and a covering solution resulting from step c) to polarized electromagnetic waves that excite the fluorophore; and
   e) determining a quantity of the particular analyte in the test sample based on measuring polarization anisotropy of fluorescent emissions directly from the substrate and the covering solution,
   wherein the detection molecule is selected so that polarization anisotropy decreases with an increase in a ratio of a number of detection molecules bound directly or indirectly to the functionalized substrate divided by a number of free detection molecules in the covering solution.

2. The method as recited in claim 1, wherein the metallic nanoparticles have diameters small compared to a wavelength of fluorescent emissions from the fluorophore.

3. The method as recited in claim 1, wherein the metallic nanoparticles are composed of a metal selected from a group comprising gold and silver and aluminum.

4. The method as recited in claim 1, wherein, during step c, a detection molecule is bound directly or indirectly to the target molecule affixed to the substrate so as to bring the fluorophore included in the detection molecule within about 50 nanometers of a metallic nanoparticle affixed to the substrate.

5. The method as recited in claim 1, wherein, determining the quantity of the particular analyte in the test sample during step c further comprises comparing the measured polarization anisotropy of fluorescent emissions to a calibration curve that associates a degree of anisotropy with the ratio.

6. The method as recited in claim 1, wherein:
   the detection molecule competes with the particular analyte for binding to the target molecule; and
   step c) further comprises contacting the functionalized substrate to a mixture of the test sample and the reagent under conditions that allow steady state binding of the particular analyte in the mixture to the target molecules,
   whereby the method is termed a competitive binding assay.

7. The method as recited in claim 1, wherein:
   the detection molecule binds to the particular analyte; and
   step c) further comprises
      contacting the functionalized substrate with the test sample under conditions that cause an amount of the particular analyte which binds to the target molecules to be proportional to an amount of the particular analyte in the sample,
      washing the functionalized substrate that has analyte bound to target molecules, and
      contacting the functionalized substrate that has analyte bound to target molecules with the reagent under conditions that allow steady state binding of the detection molecules in the reagent to the particular analyte that is bound to the target molecules affixed to the substrate,
   whereby the method is termed a sandwich binding assay.

8. The method as recited in claim 1, wherein the target molecule is selected from a group comprising a polymer, a ligand, an antigen, an antibody and a strand of deoxyribonucleic acid (DNA).

9. The method as recited in claim 1, wherein the particular analyte is selected from a group comprising a polymer, a ligand, an antigen, an antibody and a strand of deoxyribonucleic acid (DNA).

10. The method as recited in claim 1, wherein the detection molecule comprises a biomolecule selected from a group comprising a polymer, a ligand, an antigen, an antibody, a protein, an oligomer and a strand of deoxyribonucleic acid (DNA).

11. The method as recited in claim 1, wherein the fluorophore is selected from a group comprising a fluoresceins, eosin, coumarines, rhodamines, cyanines, benzophenoxazines, phycobiliproteins and fluorescent proteins.

12. The method as recited in claim 1, wherein the detection molecule comprises an intrinsically fluorescent biomolecule.

13. The method as recited in claim 12, wherein the intrinsically fluorescent biomolecule is selected from a group comprising aromatic acids, tyrosine, tryptophan, flavins and nicotinamide adenine dinucleotide hydrogenated (NADH).

14. A competitive binding assay for determining the quantity of an analyte comprising:
   a) providing a functionalized substrate that comprises metallic nanoparticles and a plurality of substantively identical bioactive target molecules affixed to a substrate, wherein the bioactive target molecule binds to a particular analyte;
b) providing a reagent comprising a plurality of substantively identical detection molecules, wherein
the detection molecule comprises a fluorophore, and
the detection molecule competes with the particular analyte for binding to the target molecule;
c) contacting the functionalized substrate to a mixture of a test sample and the reagent under conditions that allow steady state binding of the particular analyte in the mixture to the target molecules;
d) exposing the functionalized substrate and covering solution resulting from step c) to polarized electromagnetic waves having a wavelength that excites the fluorophore; and
e) determining a concentration of the particular analyte in the test sample based on measuring polarization anisotropy of fluorescent emissions directly from the substrate and the covering solution,
wherein the detection molecule is selected so that polarization anisotropy decreases with an increase in a ratio of a number of detection molecules bound directly or indirectly to the functionalized substrate divided by a number of free detection molecules in the covering solution.

15. A sandwich binding assay for determining the quantity of an analyte comprising:
a) providing a functionalized substrate that comprises metallic nanoparticles and a plurality of substantively identical bioactive target molecules affixed to a substrate, wherein the bioactive target molecule binds to a particular analyte;
b) providing a reagent comprising a plurality of substantively identical detection molecules, wherein
the detection molecule comprises a fluorophore, and
the detection molecule binds to the particular analyte;
c) contacting the functionalized substrate with a test sample under conditions that cause an amount of the particular analyte which binds to the target molecules to be proportional to an amount of the particular analyte in the sample;
d) washing the functionalized substrate that has analyte bound to target molecules;
e) contacting the functionalized substrate that has analyte bound to target molecules with the reagent under conditions that allow steady state binding of the detection molecules in the reagent to the particular analyte that is bound to the target molecules affixed to the substrate;
f) exposing the functionalized substrate and covering solution resulting from step e) to polarized electromagnetic waves that excite the fluorophore; and
g) determining a quantity of the particular analyte in the test sample based on measuring polarization anisotropy of fluorescent emissions directly from the substrate and the covering solution,
wherein the detection molecule is selected so that polarization anisotropy decreases with an increase in a ratio of a number of detection molecules bound directly or indirectly to the functionalized substrate divided by a number of free detection molecules in the covering solution.

* * * * *